Figure 3:
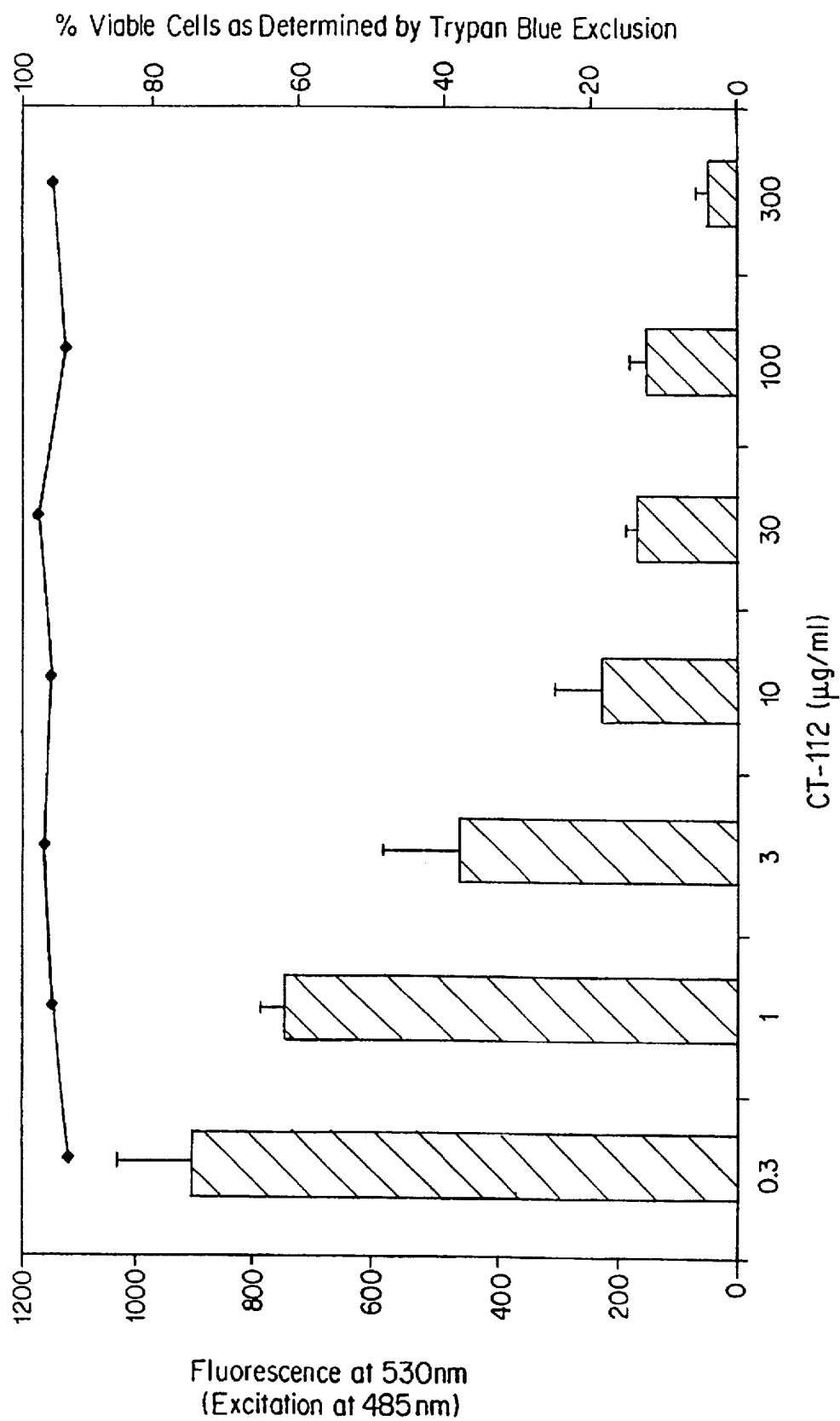

United States Patent
Counts et al.

[19]

[11] Patent Number: 5,776,892
[45] Date of Patent: Jul. 7, 1998

[54] ANTI-INFLAMMATORY PEPTIDES

[75] Inventors: David F. Counts, Coram; Ronald G. Duff, East Moriches, both of N.Y.

[73] Assignee: Curative Health Services, Inc., Hauppauge, N.Y.

[21] Appl. No.: 259,550

[22] Filed: Jun. 16, 1994

Related U.S. Application Data

[63] Continuation-in-part of Ser. No. 80,371, Jun. 18, 1993, abandoned, and a continuation-in-part of Ser. No. 37,486, Mar. 24, 1993, Pat. No. 5,470,831, which is a continuation of Ser. No. 631,823, Dec. 21, 1990, abandoned.

[51] Int. Cl.$^6$ .......................... A61K 38/07; A61K 38/08; A61K 38/12; C07K 7/06
[52] U.S. Cl. .......................... 514/11; 514/15; 514/16; 514/17; 514/18; 530/317; 530/327; 530/328; 530/329; 530/330; 530/345
[58] Field of Search .......................... 514/9, 10, 11, 514/16, 17, 18, 15; 530/317, 318, 319, 320, 321, 323, 328, 329, 330, 345, 380, 327

[56] References Cited

U.S. PATENT DOCUMENTS

| | | | |
|---|---|---|---|
| 4,461,724 | 7/1984 | Konishi | 530/350 |
| 4,585,755 | 4/1986 | Morgan et al. | 530/321 |
| 4,645,828 | 2/1987 | Twardzik | 530/324 |
| 4,703,034 | 10/1987 | Freidinger et al. | 514/11 |
| 4,719,288 | 1/1988 | Fuhrer et al. | 530/331 |
| 4,816,449 | 3/1989 | Hahn | 514/17 |
| 4,816,560 | 3/1989 | Verdini et al. | 530/332 |
| 5,086,164 | 2/1992 | Maione | 530/324 |
| 5,141,851 | 8/1992 | Brown et al. | 530/335 |
| 5,358,934 | 10/1994 | Borovsky et al. | 514/17 |
| 5,386,011 | 1/1995 | Wiedeman et al. | 530/329 |
| 5,411,942 | 5/1995 | Widmer er al. | 530/317 |
| 5,436,222 | 7/1995 | Kuna et al. | 514/12 |
| 5,470,831 | 11/1995 | Whitman et al. | 514/16 |

FOREIGN PATENT DOCUMENTS

| | | |
|---|---|---|
| 0378364 | 7/1990 | European Pat. Off. |
| WO 92/11021 | 7/1992 | WIPO |

OTHER PUBLICATIONS

Banda et al., 1982, Isolation of a nonmitogenic angiogenesis factor from wound fluid, Proc. Natl. Acad. Sci. USA 79:7773–77.

Barone et al., 1991, Polymorphonuclear Leukocyte Infiltration Into Cerebral Focal Ischemic Tissue: Myeloperoxidase Activity Assay and Histologic Verification, J. Neurosci. Res. 29:336–45.

Bebawy et al., 1986, In Vitro Effects of Platelet Factor 4 on Normal Human Neutrophil Functions, J. Leukocyte Biol. 39:423–34.

Bernstein et al., 1982, Migration of Cultured Vascular Cells in Response to Plasma and Platelet–Derived Factors, J. Cell Sci. 56:71–82.

Blackwell et al., 1980, Macrocortin: A Polypeptide Causing the Anti–phospholipase Effect of Glucocorticoids, Nature 287:147–49.

Browne & Leslie, 1976, Animal Models of Peritonitis, Surg. Gynecol. Obstet. 143:738–40.

Broxmeyer et al., 1993, Comparative Analysis of the Human Macrophage Inflammatory Protein Family of Cytokines (Chemokines) on Proliferation of Human Myeloid Progenitor Cells, J. Immunol. 150:3448–58.

Cella et al., 1986, Platelet Factor 4 (PF4) and Heparin Released Platelet Factor 4 (HR–PF4) in Diabetes Mellitus Effect of the Duration of the Disease, Folia Haematol. 113:646–54.

(List continued on next page.)

*Primary Examiner*—Jeffrey E. Russel

[57] ABSTRACT

The present invention relates to peptides, peptide analogs and peptide derivatives related to platelet factor 4 which exhibit anti-inflammatory activity, to pharmaceutical compositions comprising said peptides, and to methods of inhibiting inflammation utilizing the peptides of the invention.

24 Claims, 13 Drawing Sheets

OTHER PUBLICATIONS

Ciaglowski et al., 1986, Isolation and Amino Acid Sequence of Bovine Platelet Factor 4, Arch. Biochem. and Biophy. 250:249–56.

Cortellaro et al., 1990, High Heparin Released Platelet Factor 4 in Uncomplicated Type 1 Diabetes Mellitus, Thromb. Res. 58:571–76.

Diezel et al., 1989, Inhibition of Cutaneous Contact Hypersensitivity by Calcium Transport Inhibitors Lanthanum and Diltiazem, J. Invest. Dermatol. 93:322–26.

Doherty et al., 1988, Multiple Topical Applications of Arachidonic Acid to Mouse Ears Induce Inflammatory and Proliferative Changes, J. Invest. Derm. 91:298–302.

Edgington, 1993, Chemokines in Cardiovascular Disease, Bio/Technol. 11:676–81.

Eisman et al., 1990, Structural and Functional Comparison of the Genes for Human Platelet Factor 4 and $PF4_{alt}$, Blood 76:336–44.

Filipp et al., 1984, Effect of Highly Radiolabelled 2,4-Dinitrochlorobenzene (DNCB) on Experimental DNCB Contact Dermatitis in Guinea Pigs, Allergy 39:499–507.

Gimbrone et al., 1974, Tumor Growth and Neovascularization: An Experimental Model Using the Rabbit Cornea, J. Nat'l Cancer Inst. 52:413–427.

Griswold et al., 1991, Pharmacology of the Pyrroloimidazole, SK&F 105809–II; Antiinflammatory Activity and Inhibition of Mediator Production In Vivo, Biochem. Pharmacol. 42:825–31.

Guastamacchia et al., 1985, PF, VIII/vWF, B–TG and $PF_4$ In Diabetic Subjects, Both Type 1 and 2, With and Without Retinopathy, Boll. Soc. It. Biol. 61:499–505.

Hanna et al., 1990, Pharmacological Profile of SK&F 105809, A Dual Inhibitor of Arachidonic Acid Metabolism, Drugs Exptl. Clin. Res. 16:137–47.

Johansson et al., 1993, Speculations around the Mechanism behind the Action of Peptide T in the Healing of Psoriasis: A Minireview, Acta Derm Venereol (Stockh) 73:401–403.

Johansson et al., 1994, Somatostatin Immunoreactive Cells in Lesional Psoriatic Human Skin during Peptide T Treatment, Acta Derm Venereol (Stockh) 74:106–109.

Kragballe & Voorhees, 1985, Arachidonic Acid and Leukotrienes in Clinical Dermatology, Curr. Probl. Derm. 13:1–10.

Medici et al., 1989, Improved Method for Purification of Human Platelet Factor 4 by Affinity and Ion–Exchange Chromatography, Thromb. Res. 54:277–87.

Obal et al., 1990, Interleukin 1α and an interleukin 1β fragment are somnogenic, Am. J. Physiol. 259:R439–46.

Rybak et al., 1989, Interaction of Platelet Factor Four With Cultured Vascular Endothelial Cells, Blood 73:1534–39.

Schmitz–Huebner & Knop, 1984, Evidence for an Endothelial Cell Dysfunction in Association with Behcet's Disease, Thromb. Res. 34:277–85.

Weerasinghe et al., 1984, Inhibition of the Cerebroside Sulphate (Sulphatide)–Induced Contact Activation Reactions by Platelet Factor Four, Thromb. Res. 33:625–31.

Wei & Thomas, 1993, Anti–Inflammatory Peptide Agonists, Annu. Rev. Pharmacol. Toxicol. 33:91–108.

Wooley, 1988, Collagen–Induced Arthritis in the Mouse, Meth. Enzym. 162:361–73.

Young et al., 1984, The Mouse Ear Inflammatory Response to Topical Arachidonic Acid, J. Invest. Derm. 82:367–71.

Zucker et al., 1989, Immunoregulatory Activity of Peptides Related to Platelet Factor 4, Proc. Natl. Acad. Sci. USA 86:7571–74.

1    Thr Thr Ser Gln Val Arg Pro Arg
2  Val Lys Thr Thr Ser Gln Val Arg Pro Arg
3            Ser Gln Val Arg Pro Arg
4                Val Arg Pro Arg
5    Thr Thr Ser Gln Val Arg Pro Arg His Ile Thr
6    Thr Thr Ser Gln Val
7        Thr Ser Gln Val Arg
8    Thr Thr Ser Gly Ile His Pro Lys

FIG.1

```
                    5                      10                      15
    Glu Ala Glu Glu Asp Gly Asp Leu Gln Cys Leu Cys Val Lys
Thr Thr Ser Gln Val Arg Pro Arg His Ile  Thr Ser Leu Glu Val
Ile Lys Ala Gly Pro His Cys Pro Thr Ala Gln Leu Ile  Ala Thr
Leu Lys Asn Gly Arg Lys Ile  Cys Leu Asp Leu Gln Ala Pro Leu
Tyr Lys Lys Ile  Ile  Lys Lys Leu Leu Glu Ser
```

FIG. 2

ANTI-INFLAMMATORY PEPTIDES

CROSS-REFERENCE TO RELATED APPLICATIONS

This application is a continuation-in-part of application Ser. No. 08/080,371 filed Jun. 18, 1993 now abandoned, and is a continuation-in-part of application Ser. No. 08/037,486 filed Mar. 24, 1993 currently U.S. Pat. No. 5,470,831, which is a continuation of application Ser. No. 07/631,823 filed Dec. 21, 1990, now abandoned, the entire disclosure of which are incorporated herein by reference.

1. INTRODUCTION
2. BACKGROUND OF THE INVENTION
  2.1. PLATELET FACTOR 4
  2.2. INFLAMMATION
3. SUMMARY OF THE INVENTION
4. DESCRIPTION OF THE FIGURES
5. DETAILED DESCRIPTION OF THE INVENTION
  5.1. PREPARATION OF PLATELET FACTOR 4
  5.2. PEPTIDES OF THE INVENTION AND THEIR PREPARATION
  5.3. IDENTIFICATION OF ANTI-INFLAMMATORY PEPTIDES
  5.4. THE USE OF PEPTIDES OF THE INVENTION AS ANTI-INFLAMMATORY AGENTS
6. EXAMPLE: PREPARATION OF ANTI-INFLAMMATORY PEPTIDES
  6.1. MATERIALS AND METHODS
    6.1.1. PREPARATION OF PF4
    6.1.2. TRYPTIC DIGESTION OF PF4
  6.2. RESULTS AND DISCUSSION
7. EXAMPLE: CT-112 EXHIBITS ANTI-INFLAMMATORY ACTIVITY
  7.1. MATERIALS AND METHODS
    7.1.1. REAGENTS
    7.1.2. ANIMAL TREATMENT
  7.2. RESULTS AND DISCUSSION
8. EXAMPLE: CT-112 INHIBITION OF NEUTROPHIL CHEMOTAXIS
  8.1. MATERIALS AND METHODS
  8.2. RESULTS AND DISCUSSION
49. EXAMPLE: EFFECT OF DURATION OF EXPOSURE TO CT-112
  9.1. MATERIALS AND METHODS
  9.2. RESULTS AND DISCUSSION
10. EXAMPLE: EFFECT OF INTRAPERITONEAL INJECTION OF CT-112
  10.1. MATERIALS AND METHODS
  10.2. RESULTS AND DISCUSSION
11. EXAMPLE: EFFECT OF SUBCUTANEOUS INJECTION OF CT-112
  11.1. MATERIALS AND METHODS
  11.2. RESULTS AND DISCUSSION
12. EXAMPLE: EFFECT OF ORAL ADMINISTRATION OF CT-112
  12.1. MATERIALS AND METHODS
  12.2. RESULTS AND DISCUSSION
13. EXAMPLE: EFFECT OF CT-112 ON THE CARAGEENAN-INDUCED MODEL OF PERITONITIS
  13.1. MATERIALS AND METHODS
  13.2. RESULTS AND DISCUSSION
14. EXAMPLE: STRUCTURE ACTIVITY RELATIONSHIPS
  14.1 COMPARISON OF ANTI-INFLAMMATORY ACTIVITIES OF CT-114 AND CT-112
    14.1.1. MATERIALS AND METHODS
    14.1.2. RESULTS AND DISCUSSION
  14.2. ANTI-INFLAMMATORY ACTIVITY OF OTHER PEPTIDES
    14.2.1. MATERIALS AND METHODS
    14.2.2. RESULTS AND DISCUSSION
  14.3. ANTI-INFLAMMATORY ACTIVITY OF BLOCKED, SUBSTITUTED AND TRUNCATED VERSIONS OF CT-112
    14.3.1. MATERIALS AND METHODS
    14.3.2. RESULTS AND DISCUSSION
15. EXAMPLE: EFFECT OF CT-112 ON DELAYED-TYPE HYPERSENSITIVITY
  15.1. MATERIALS AND METHODS
  15.2. RESULTS AND DISCUSSION
16. EXAMPLE: EFFECT OF CT-112 ON TYPE-II COLLAGEN IMMUNIZATION INDUCED RHEUMATOID ARTHRITIS
  16.1. MATERIALS AND METHODS
  16.2. RESULTS AND DISCUSSION
17. EXAMPLE: TOXICITY STUDIES

1. INTRODUCTION

The present invention relates to peptides and peptide derivatives related to platelet factor 4 (SEQ. ID NO: 9), and analogous peptides, which exhibit anti-inflammatory activity, to pharmaceutical compositions comprising said peptides, and to methods of inhibiting inflammation utilizing the peptides of the invention.

2. BACKGROUND OF THE INVENTION

2.1. Platelet Factor 4

Platelet factor 4 (PF4) (SEQ. ID NO: 9), a 70 amino acid heparin-binding protein, is released from the alpha granules of activated platelets. The exact biological function of PF4 (SEQ. ID NO: 9) is not known, although PF4 (SEQ. ID NO: 9) is a member of a multigene family involved in chemotaxis, coagulation, inflammation, and cell growth (Eisman et al., 1990, Blood 76:336–344). The genomic sequence (SEQ. ID NO: 9) of the PF4 gene, and a highly homologous gene, PF4 alt, has recently been reported (Eismann et al., supra). Among the reported biological activities of PF4 (SEQ. ID NO: 9) are alleviation of concanavalin A-induced immunosuppression in mice (Zucker et al., 1989, Proc. Natl. Acad. Sci. 86:7571–7574); the ability to bind to and enter endothelial cells (Rybak et al., 1989, Blood 73:1534–1539); the elicitation of neutrophil chemotaxis, lysosomal enzyme release and increased adherence (Bebawy et al., 1986, J. Leukocyte Biol. 39:423–434); stimulation of migration of pericytes but not of smooth muscle cells nor endothelial cells (Bernstein et al., 1982, J. Cell. Sci. 56:71–82); and a potential anti-thrombotic effect (Weerasinghe et al., 1984, Thromb. Res. 33:625–632). Increased levels of PF4 (SEQ. ID NO: 9) have been identified in diabetic patients (Guastamacchia et al., 1985, Boll. Soc. Ital. Biol. Sper. 61:499–502; Cortellaro et al., 1990, Thromb. Res. 58:571–576; Cella et al., 1986, Folia Haematol. 113:646–654) and in patients with Behcet's disease (Schmitz-Huebner and Knap, 1984, Thromb. Res. 34:277–286).

2.2. Inflammation

Dermal inflammation is partially mediated via the conversion of phospholipids to either endoperoxides and consequently prostaglandins via cyclooxygenase or 5-HETEs and consequently leukotrienes via lipoxygenase (Kragball and Voorhees, 1985, Curr. Probl. Derm. 13:1–10). Inhibition of either or both of these pathways is the means by which non-steroidal anti-inflammatory agents prevent an inflammatory response. Anti-inflammatory steroids act by inhibiting the release of arachidonic acid which can then be converted via either pathway to mediators of inflammation (Blackwell et al., 1980, Nature 287:147–149). It has been proposed that cytokines also mediate the inflammatory process and a better, or at least, equivalent inhibition of the inflammatory response may be achieved by inhibiting either cytokine production or the inhibition of the interaction of cytokines with their receptors on the cell surface of the inflammatory cell infiltrate.

Within the past few years it has been recognized that different domains on cytokines are able to induce different physiological responses, as illustrated by the example of IL-1β fragments. The somnogenic and pyrogenic properties of IL-1β reside in the fragment IL-1β(208–240), whereas other distinct and separate fragments of IL-1β stimulate T-cell production (Obal et al., 1990, Am. J. Physiol. 259:R439–R446).

3. SUMMARY OF THE INVENTION

The present invention relates to peptides and peptide derivatives related to platelet factor 4 (PF4) (SEQ. ID NO: 9), and analogous peptides, which exhibit anti-inflammatory activity, to pharmaceutical compositions comprising said peptides, and to methods for inhibiting inflammation utilizing said peptides. The invention is based in part on the discovery that the octapeptide CT-112 (SEQ. ID NO: 1), and derivatives and analogs of CT-112 (SEQ. ID NO: 1), have anti-inflammatory activity in the mouse ear/arachidonic acid model of inflammation.

The peptides of the invention, particularly CT-112 (SEQ. ID NO: 1), may be particularly useful to inhibit an inflammatory response. For example, but not by way of limitation, CT-112 (SEQ. ID NO: 1) or analogs or derivatives thereof may be used to inhibit inflammation in autoimmune diseases;, graft versus host disease, reperfusion injury, atherosclerosis, and asthma.

4. DESCRIPTION OF THE FIGURES

FIG. 1. Amino acid sequences of anti-inflammatory peptides CT-112 (SEQ. ID NO: 1) and peptides previously designated as Wohl-2 through Wohl-8 (SEQ. ID NOS: 2–8).

FIG. 2. Amino acid sequence of mature PF4 (SEQ. ID NO: 9).

FIG. 3. Effects of CT-112 (SEQ. ID NO: 1) on neutrophil cells. Bar graph showing effect of CT-112 (SEQ. ID NO: 1) on chemotaxis of neutrophils to f-Met-Leu-Phe, as measured by fluorescence at 530 nm. Line graph showing effect of CT-112 (SEQ. ID NO: 1) on cell viability, as measured using trypan blue exclusion. Bar graph values represent the mean ±SD of three wells.

Figure 4:
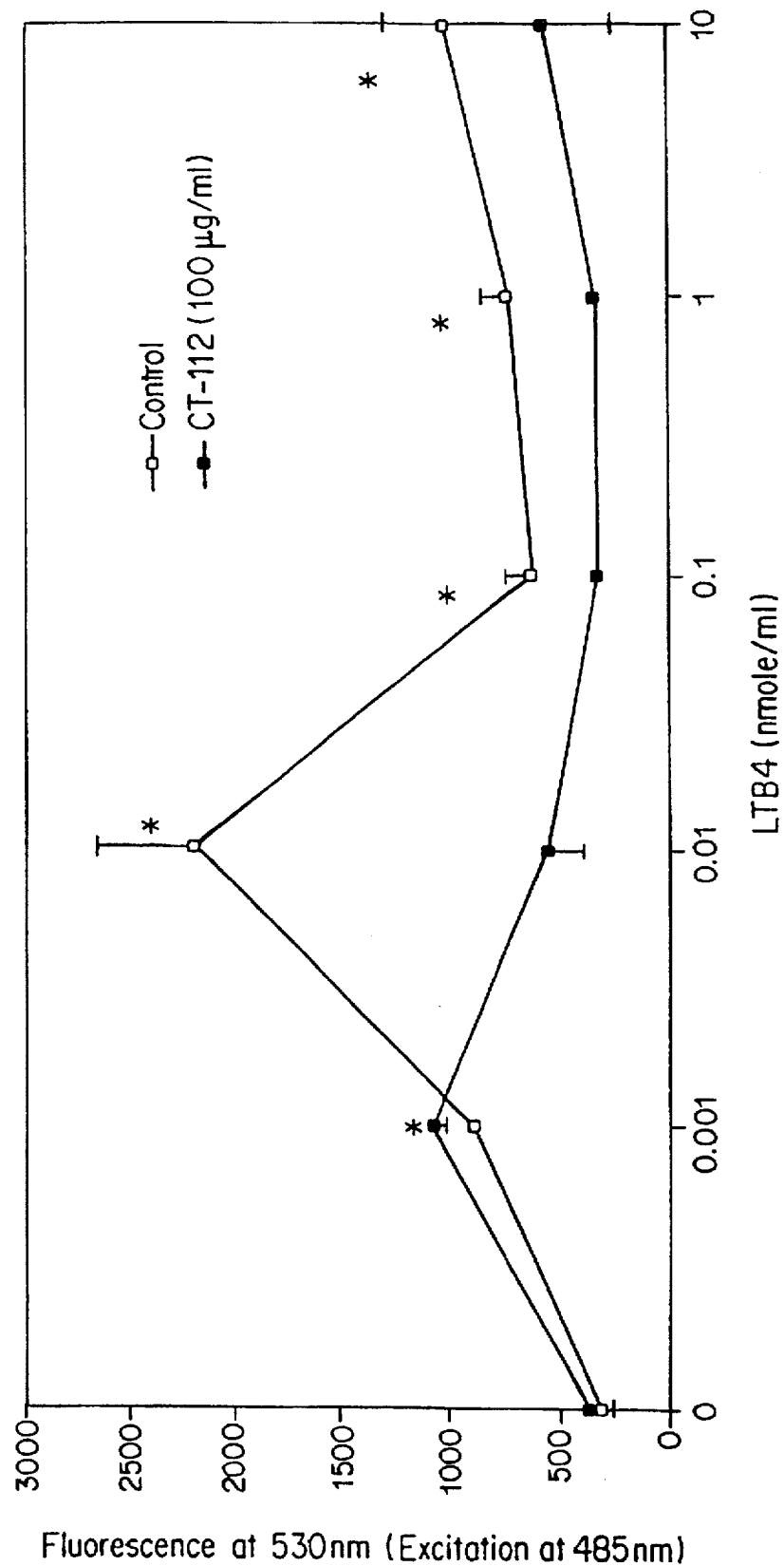

FIG. 4. Effect of CT-112 (SEQ. ID NO: 1) on chemotaxis of neutrophils to leukotriene $B_4$ ($LTB_4$), as measured by fluorescence at 530 nm. Values represent the mean ±SD of three wells.

Figure 5:
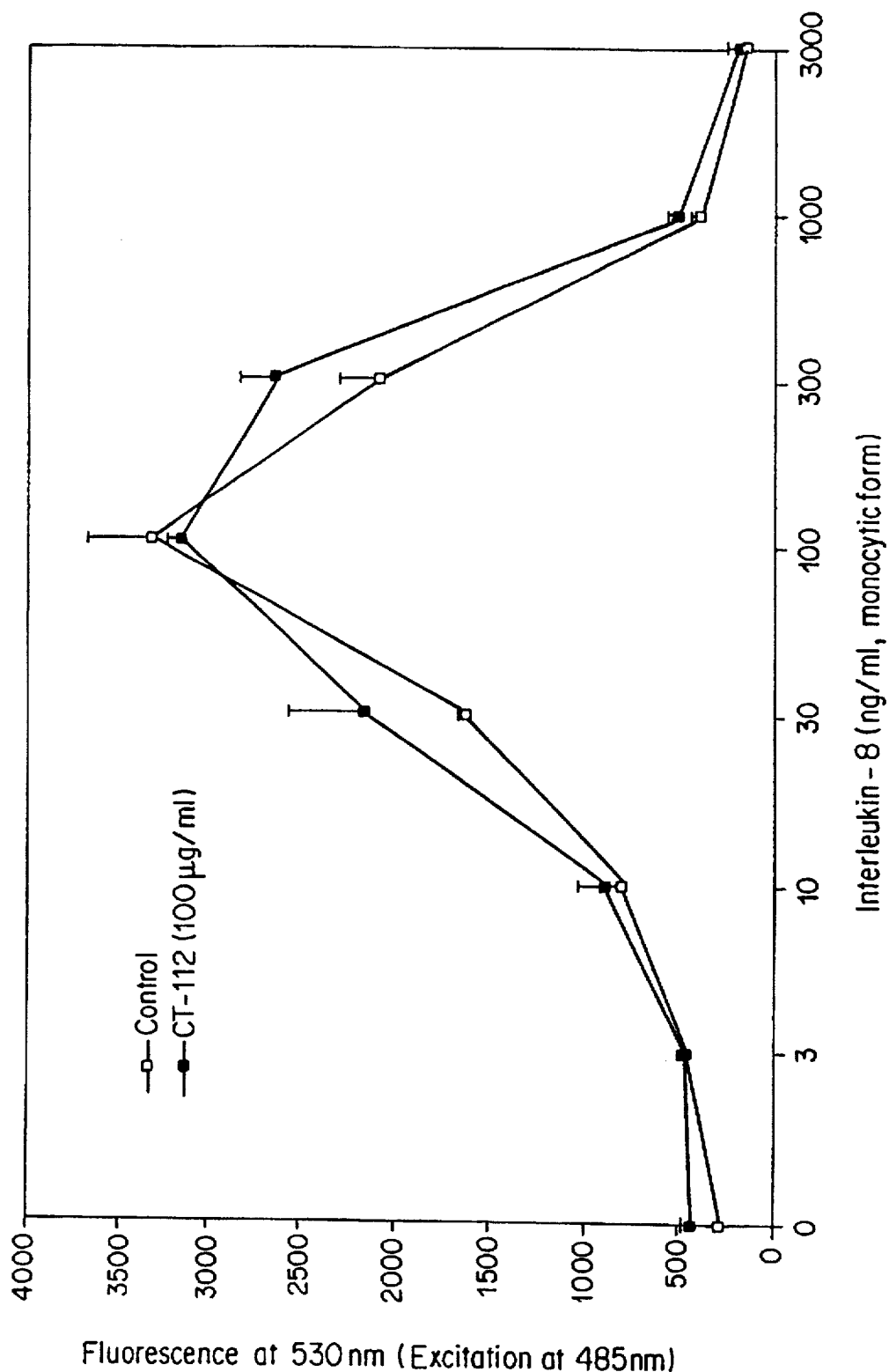

FIG. 5. Effect of CT-112 (SEQ. ID NO: 1) on chemotaxis of neutrophils to Interleukin-8, as measured by fluorescence at 530 nm. Values represent the mean ±SD of three wells.

Figure 6:
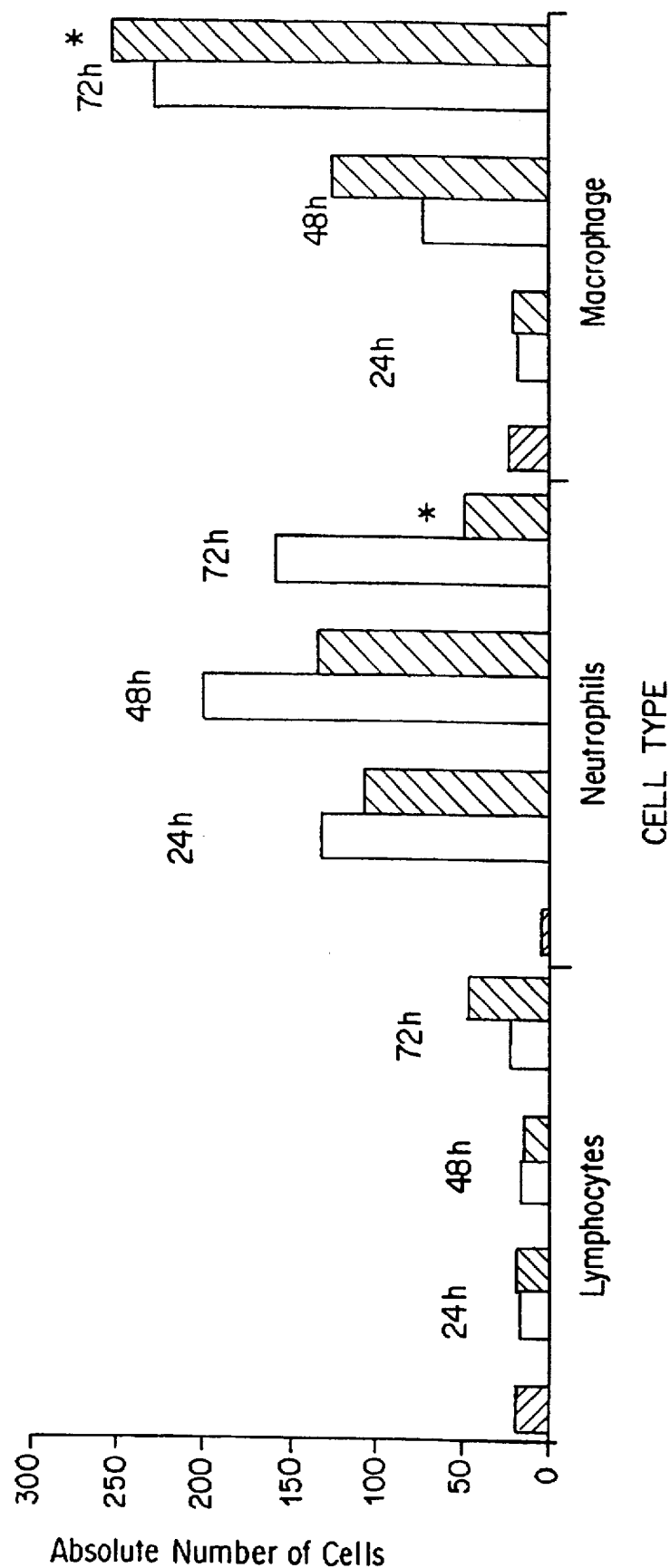

FIG. 6. Effect of CT-112 (SEQ. ID NO: 1) on carageenan-induced inflammatory cell influx. ▓, normal; □, carageenan only; ■, carageenan plus CT-112 (SEQ. ID NO: 1). * indicates significantly different ($p \leq 0.05$) from carageenan-treated control animals at the same time point.

Figure 7:
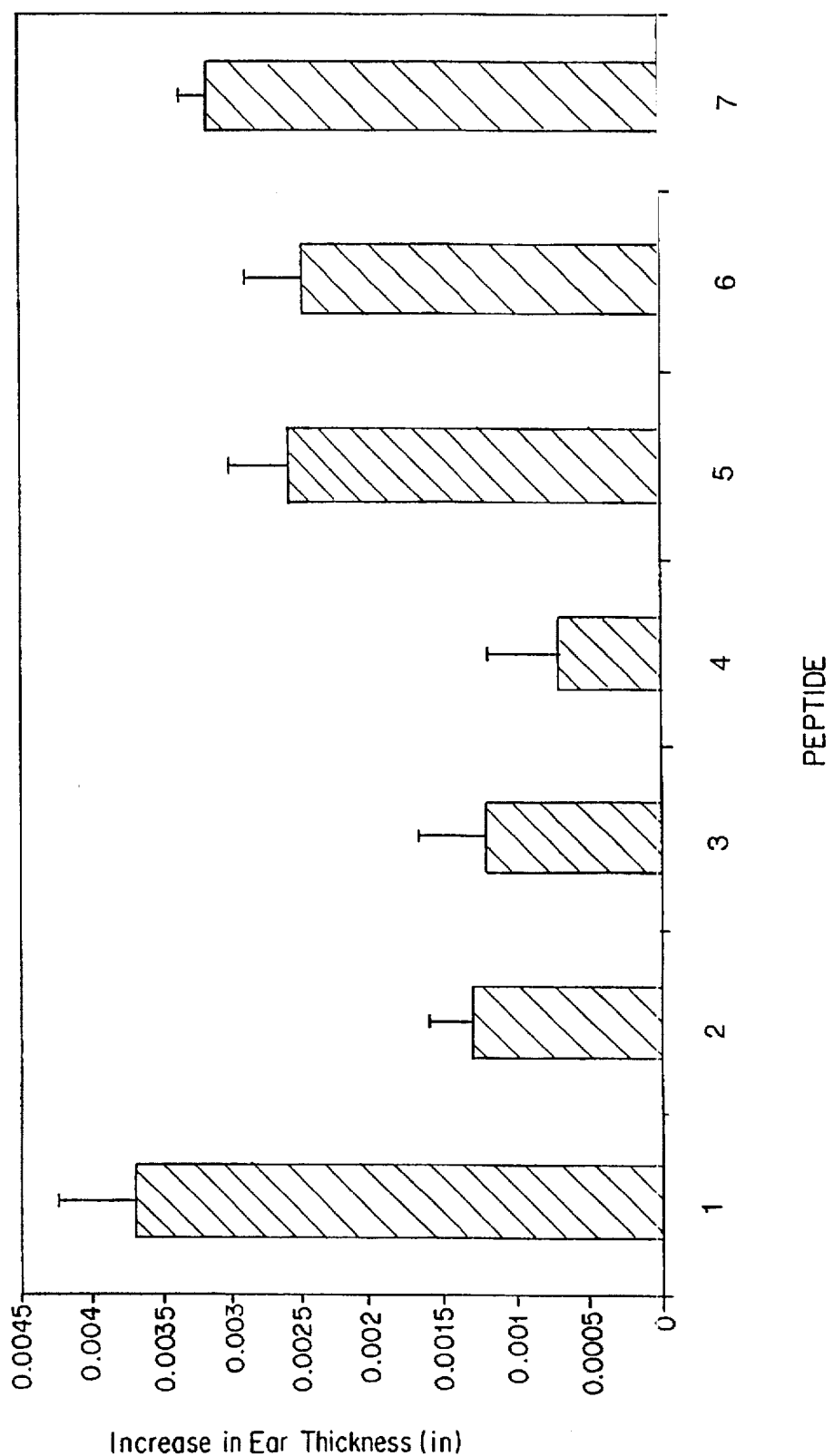

FIG. 7. Anti-inflammatory activity, as measured by inhibition of AA-induced increase in mouse ear thickness, of CT-112 (SEQ. ID NO: 1), derivatives of CT-112 (SEQ. ID NO: 1) and other peptides. 1=no treatment; 2=Thr-Thr-Ser-Gln-Val-Arg-Pro-Arg (SEQ. ID NO: 1)=CT-112; 3=Val-Thr-Arg-Pro-Thr-Gln-Arg-Ser (SEQ. ID NO: 11)=CT-120, a random octapeptide; 4=Thr-Thr-Ser-Gly-Ile-His-Pro-Lys (SEQ. ID NO: 12)=CT-127, a peptide derived from connective tissue activating peptide III (CTAP-III); 5=Ac-Thr-Thr-Ser-Gln-Val-Arg-Pro-Arg (SEQ ID NO 85)=derivative of CT-112 (SEQ. ID NO: 1) with acetyl group blocking amino terminal end; 6=Thr-Thr-Ser-Gln-Val-Arg-Pro-Arg-$NH_2$ (SEQ ID NO 86)=derivative of CT-112 (SEQ. ID NO: 1) with amido group blocking carboxyl terminal end; 7=Ac-Thr-Thr-Ser-Gln-Val-Arg-Pro-Arg-$NH_2$ (SEQ ID NO 87)= derivative of CT-112 (SEQ. ID NO: 1) with acetyl group blocking amino terminal end and amido group blocking carboxyl terminal end.

Figure 8:
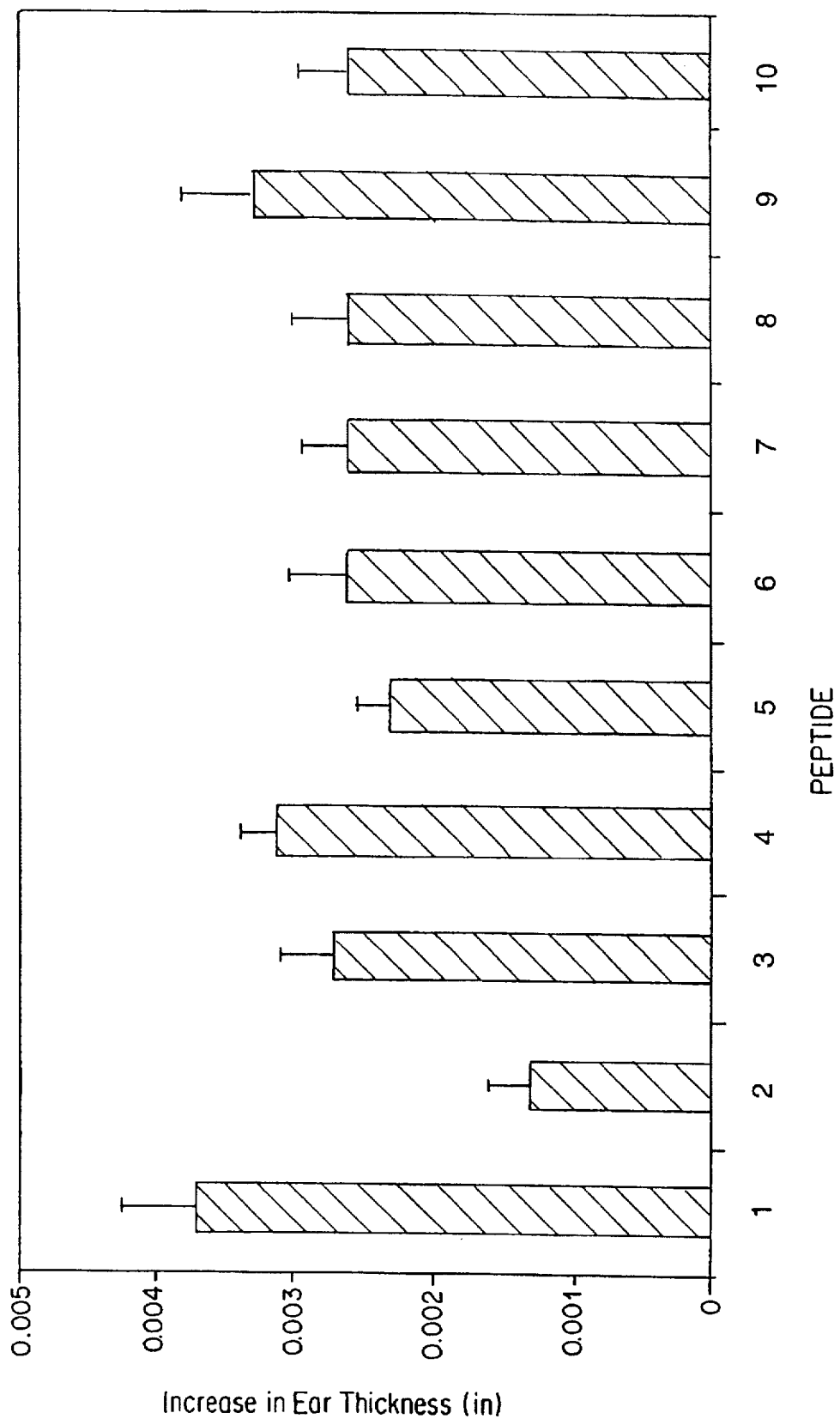

FIG. 8. Anti-inflammatory activity, as measured by inhibition of AA-induced increase in mouse ear thickness, of truncated derivatives (SEQ. ID NOS: 3, 4, 6, 24–28) of CT-112 (SEQ. ID NO: 1). 1=no treatment; 2=Thr-Thr-Ser-Gln-Val-Arg-Pro-Arg (SEQ. ID NO: 1); 3=Thr-Ser-Gln-Val-Arg-Pro-Arg (SEQ. ID NO: 25); 4=Ser-Gln-Val-Arg-Pro-Arg (SEQ. ID NO: 3); 5=Gln-Val-Arg-Pro-Arg (SEQ. ID NO: 24); 6=Val-Arg-Pro-Arg (SEQ. ID NO: 4); 7=Thr-Thr-Ser-Gln-Val-Arg-Pro (SEQ. ID NO: 26); 8=Thr-Thr-Ser-Gln-Val-Arg (SEQ. ID NO: 27); 9=Thr-Thr-Ser-Gln-Val (SEQ. ID NO: 6); 10=Thr-Thr-Ser-Gln (SEQ. ID NO: 28).

Figure 9:
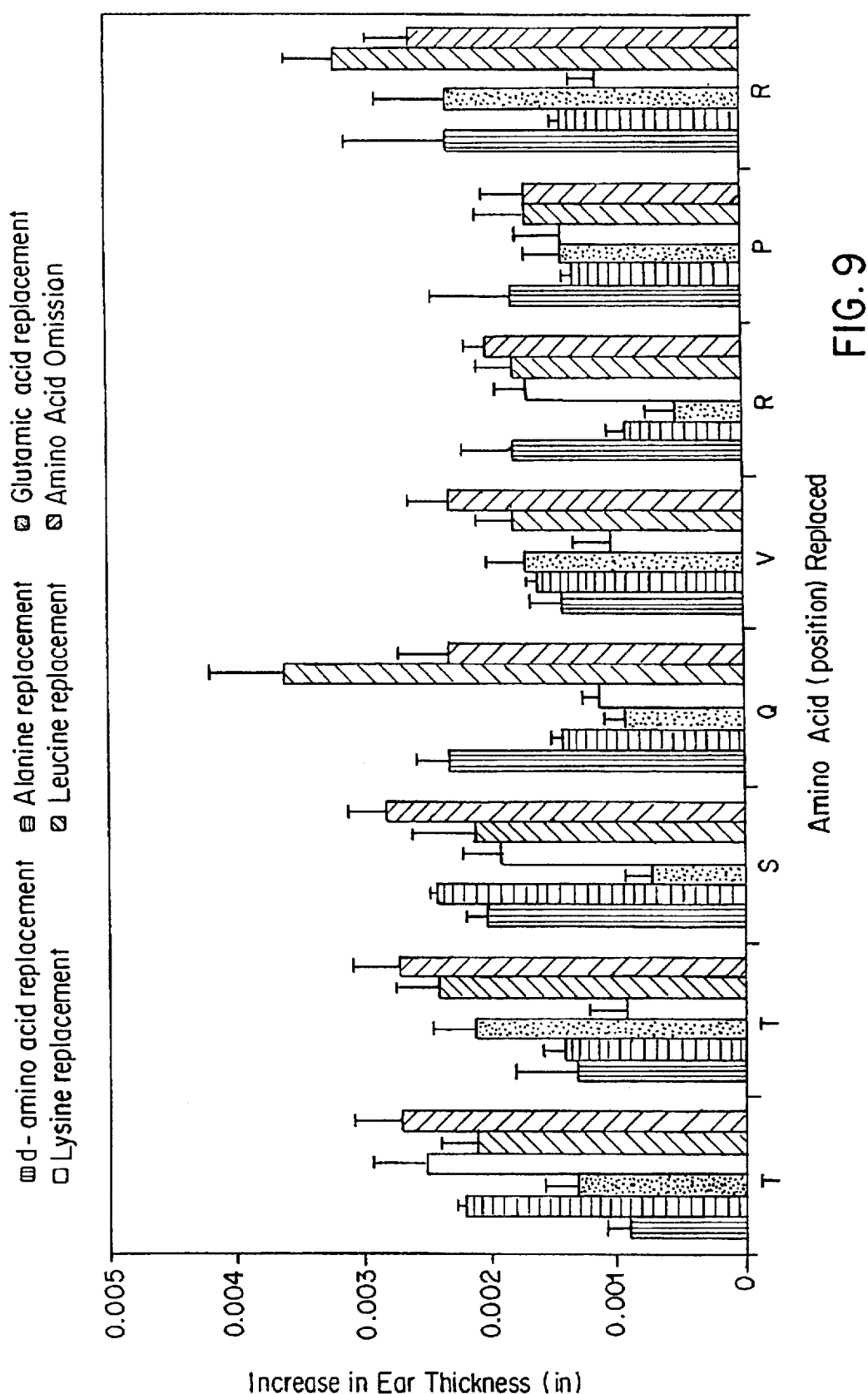

FIG. 9. Anti-inflammatory activity, as measured by inhibition of AA-induced increase in mouse ear thickness, of analogs (SEQ. ID NOS: 25, 26, 29–73) of CT-112 (SEQ. ID NO: 1).

Figure 10:
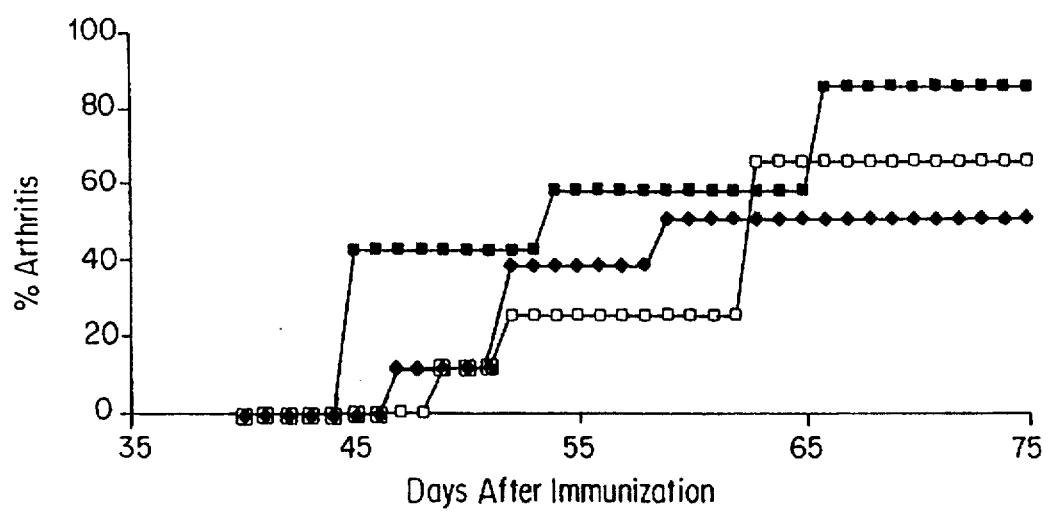

FIG. 10. Effect of CT-112 (SEQ. ID NO: 1) on percent of mice developing collagen-induced arthritis.

Figure 11:
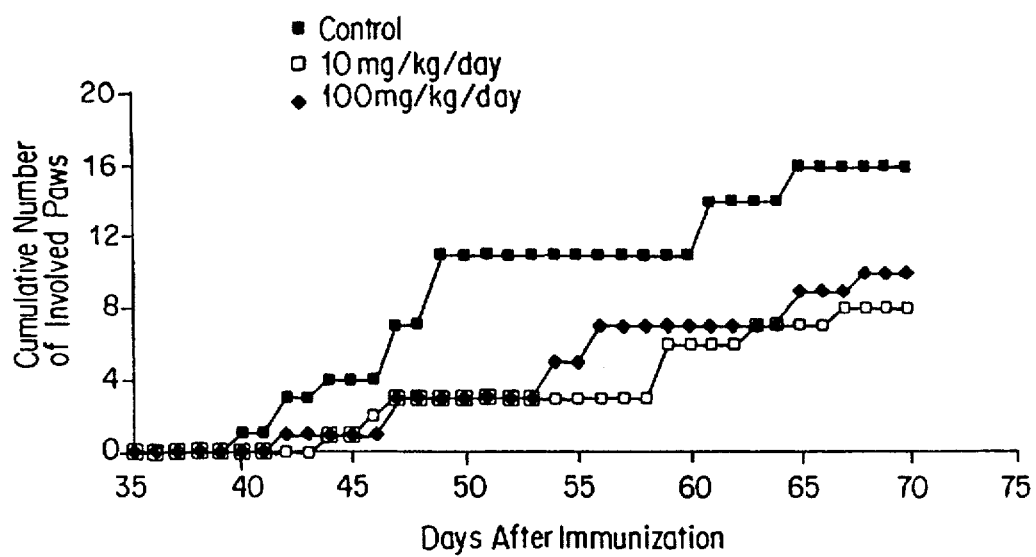

FIG. 11. Effect of CT-112 (SEQ. ID NO: 1) on the cumulative number of involved paws in mice developing collagen-induced arthritis.

Figure 12:
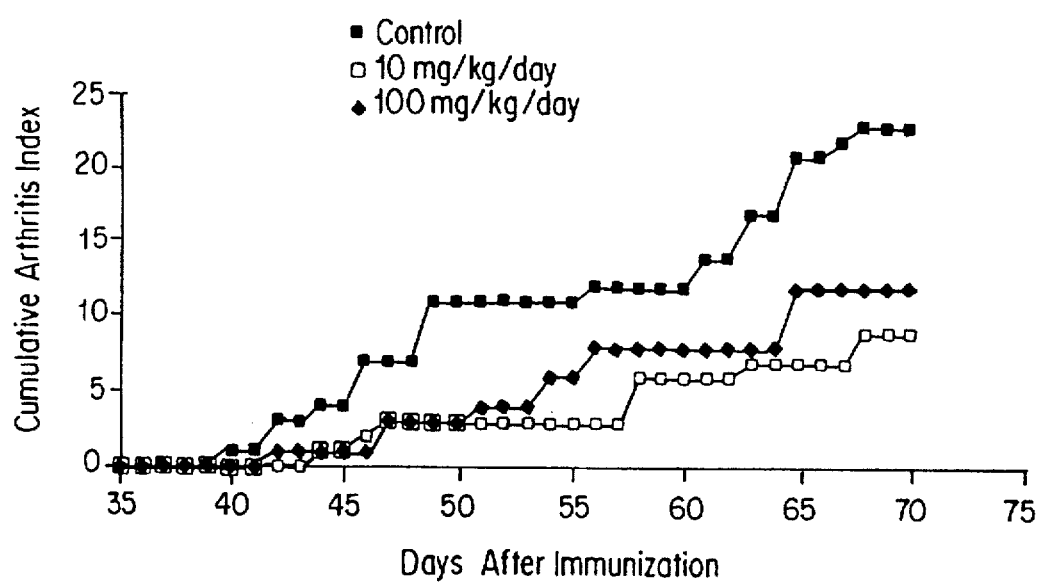

FIG. 12. Effect of CT-112 (SEQ. ID NO: 1) on the cumulative arthritis index in mice developing collagen-induced arthritis.

Figure 13:
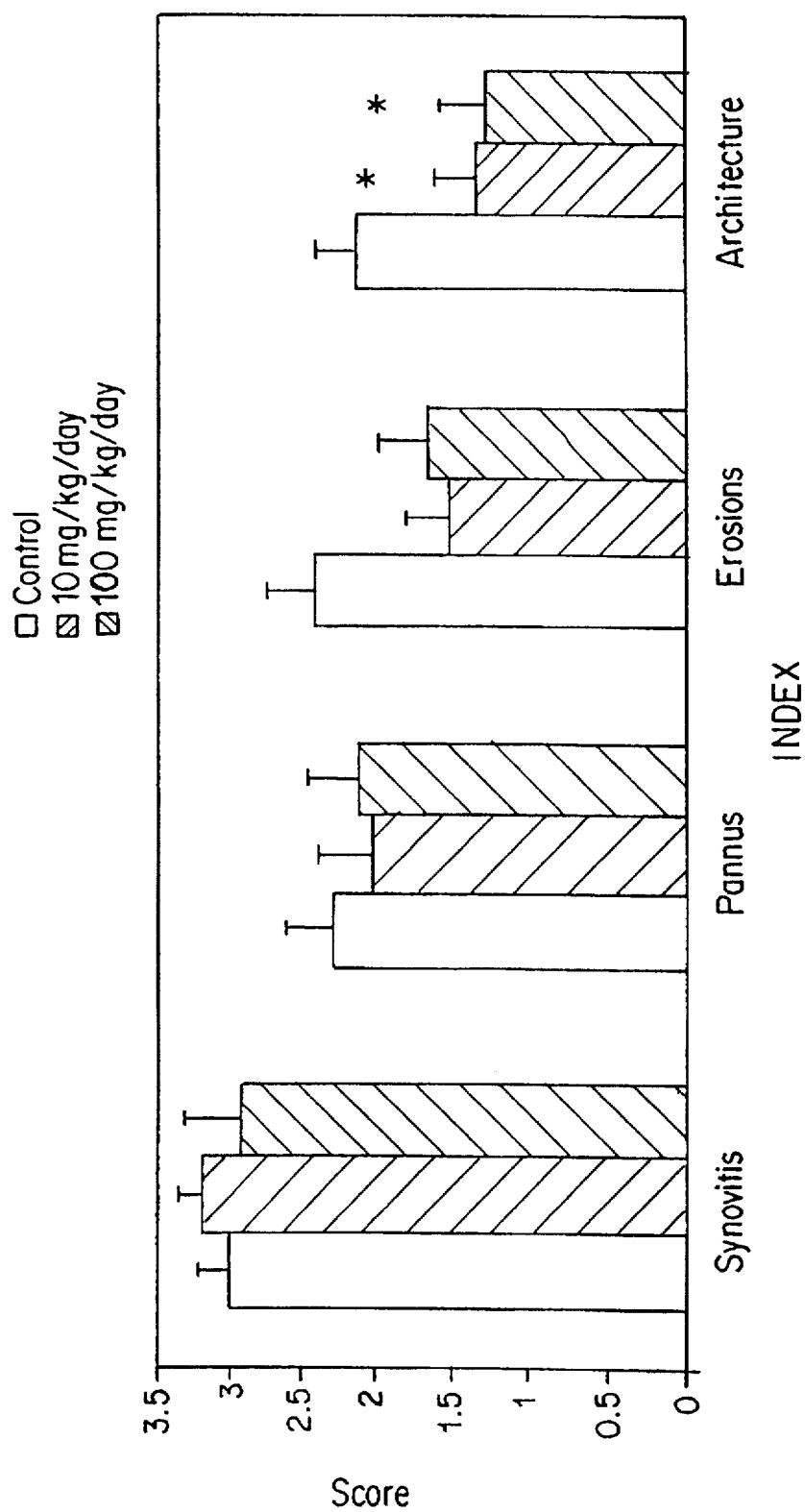

FIG. 13. Effect of CT-112 (SEQ. ID NO: 1) on the histopathology of collagen-induced arthritis in mice. Values represent the mean ±SEM of 23 paws from the control group, 26 paws from the group treated with 10 mg CT-112/kg, and 16 paws from the group treated with 100 mg CT-112/kg. * Indicates significantly different ($p \leq 0.05$) from the control group.

Figure 14:
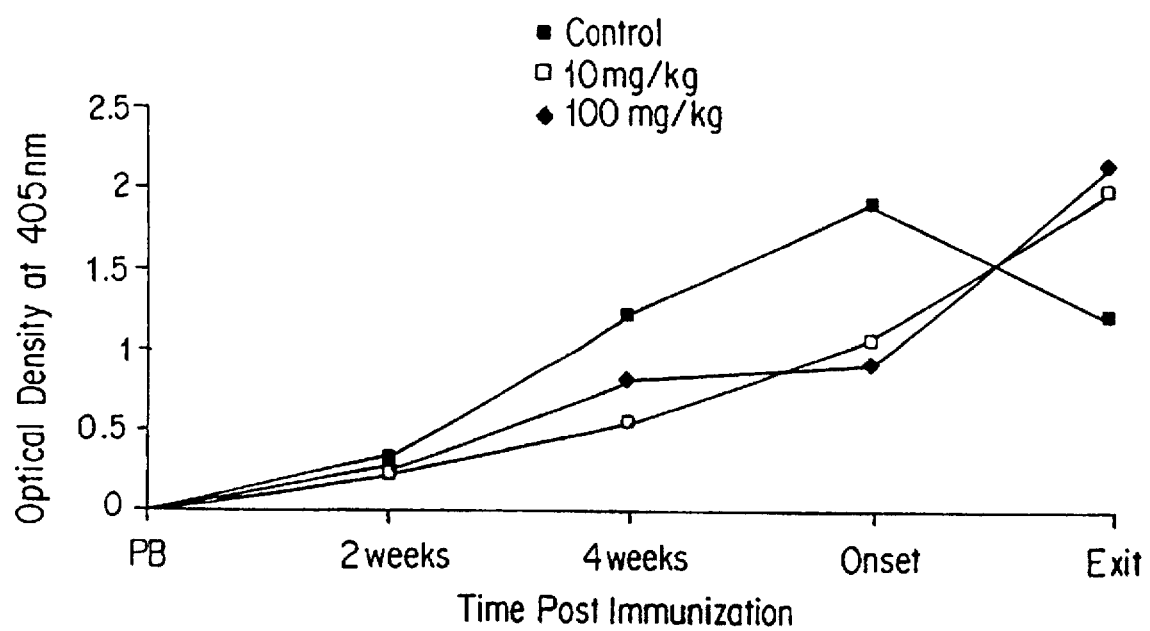

FIG. 14. Effect of CT-112 (SEQ. ID NO: 1) on circulating anti-collagen antibodies in mice immunized with collagen, as measured by O.D. at 405 nm.

5. DETAILED DESCRIPTION OF THE INVENTION

For purposes of clarity of disclosure, and not by way of limitation, the detailed description of the invention is presented in the following subsections:

(i) preparation of platelet factor 4 (SEQ. ID NO: 9);

(ii) peptides of the invention and their preparation;

(iii) identification of anti-inflammatory peptides; and (iv) the use of peptides of the invention as anti-inflammatory agents.

5.1. Preparation of Platelet Factor 4

Platelet factor 4 (PF4) (SEQ. ID NO: 9) may be purified using any method known in the art. In a preferred embodiment of the invention, PF4 (SEQ. ID NO: 9) may be purified from thrombin-activated platelet extracts by a modification of the method described by Medici, et al. (1989, Thrombos. Res. 54:277–287). PF4 (SEQ. ID NO: 9) may be isolated by heparin sepharose affinity chromatography with elution of the factor at 1.7 M NaCl, followed by strong ion exchange chromatography on a polysulfoethyl-aspartamide column eluted with NaCl in the presence of about 15% acetonitrile, and finally by separation on a Vydac RPC$_4$ reverse phase HPLC analytical column eluted with a linear acetonitrile gradient in about 0.1% trifluoroacetic acid (TFA) in water.

5.2. Peptides of the Invention and Their Preparation

The peptides of the invention include any peptide, peptide derivative or peptide analog which comprises either: (i) at least a four amino acid portion of PF4 (SEQ. ID NO: 9), the amino acid sequence (SEQ. ID NO: 9) of which is set forth in FIG. 2, or a functionally equivalent sequence; or (ii) at least a six amino acid sequence which is at least 66% homologous to a portion of the PF4 sequence (SEQ. ID NO: 9) as set forth in FIG. 2, or a functionally equivalent sequence. Homology is to be construed herein as referring to identity between amino acid residues shared by different peptides; e.g., a six amino acid residue peptide which is 66% homologous to a six amino acid fragment of PF4 shares 4 amino acid residues with the PF4 (SEQ. ID NO: 9) fragment which are not necessarily linked together.

In preferred embodiments of the invention, the peptide, peptide derivative or peptide analog comprises the sequence Thr-Ser-Gln and/or Val-Arg-Pro, and more preferably Thr-Thr-Ser-Gln (SEQ. ID NO: 10) and/or Val-Arg-Pro-Arg (SEQ. ID NO: 4) (previously designated as "Wohl-4"), or Thr-Thr-Ser-Gln-Val-Arg-Pro-Arg (SEQ. ID NO: 1). In a particularly preferred embodiment, the peptide is Thr-Thr-Ser-Gln-Val-Arg-Pro-Arg (SEQ. ID NO: 1) (i.e., "CT-112"). In additional preferred embodiments, the peptide, peptide derivative or peptide analog comprises the sequence Val-Lys-Thr-Thr-Ser-Gln-Val-Arg-Pro-Arg (SEQ. ID NO: 2) (previously "Wohl-2"), or Ser-Gln-Val-Arg-Pro-Arg (SEQ. ID NO: 3) (previously "Wohl-3"), or Thr-Thr-Ser-Gln-Val-Arg-Pro-Arg-His-Ile-Thr (SEQ. ID NO: 5) (previously "Wohl-5"), or Thr-Thr-Ser-Gln-Val (SEQ. ID NO: 6) (previously "Wohl-6"), or Thr-Ser-Gln-Val-Arg (SEQ. ID NO: 7) (previously "Wohl 7"), or Thr-Thr-Ser-Gly-Ile-His-Pro-Lys (SEQ. ID NO: 8) (previously "Wohl-8") (FIG. 1).

The peptides of the invention may also comprise portions which bear little or no homology to PF4 (SEQ. ID NO: 9) (e.g., carrier proteins). Furthermore, these peptides may be derivatized by conjugation to other compounds, including, but not limited to, carbohydrate, lipid, phosphate, starch, antibody, Fab, Fab$_2$, enzyme, amino acid, peptide, or growth factor compounds.

The amino acid sequence (SEQ. ID NO: 9) of PF4 as set forth in FIG. 2, or a functionally equivalent sequence, should be construed to mean that the PF4 sequence (SEQ. ID NO: 9) may be (i) that sequence (SEQ. ID NO: 9) set forth in FIG. 2 or (ii) the sequence (SEQ. ID NO: 9) as set forth in FIG. 2 but in which certain residues are substituted by functionally equivalent amino acids resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In other embodiments, the present invention provides for analogs and/or derivatives of CT-112 (SEQ. ID NO: 1) as anti-inflammatory agents, such as those in which the amino-terminal end of the peptide is modified by addition of an R—(C=O)— group in which R is selected from the group consisting of a lower alkyl, a cycloalkyl, an aryl and a heteroaryl, wherein the aryl or heteroaryl is either unsubstituted or substituted with a halogen, methoxy, amino or alkyl functional group, or in which the carboxyl-terminal end of the peptide is modified by addition of an R'-group in which R' is selected from the group consisting of an amide, a lower alkyl ester, a cycloalkyl ester, an aryl ester and a heteroaryl ester, wherein the aryl ester or heteroaryl ester is either unsubstituted or substituted with a halogen, methoxy, amino or alkyl functional group, or in which both ends of the peptide are so modified, provided that said analogs and/or derivatives exhibit anti-inflammatory activity, e.g., as determined by assays set forth in Section 5.3. infra. As used herein, the terms "lower alkyl" and "lower alkyl ester" are intended to encompass groups comprising from 1 to 6 carbon atoms. As used herein, the terms "aryl" and "aryl ester" are intended to encompass groups containing a 6- or 7-unit ring structure, and include, e.g., pyridinium, imidazolium and quinoxaline groups.

In other embodiments, the present invention provides for derivatives of CT-112 (SEQ. ID NO: 1) as anti-inflammatory agents in which any one or more side chain amine groups are derivatized by acylation or arylation, or in which any one or more side chain hydroxyl groups are derivatized by addition of an alkyl ester or aryl ester, or in which both amine and hydroxyl side chain groups are so derivatized, provided that said derivatives exhibit anti-inflammatory activity, e.g., as determined by assays set forth in Section 5.3. infra.

In other embodiments, the present invention provides for derivatives of CT-112 (SEQ. ID NO: 1) as anti-inflammatory agents in which CT-112 (SEQ. ID NO: 1), or a portion thereof, is cyclized by covalent linkage between non-adjacent residues, provided that said derivatives exhibit anti-inflammatory activity, e.g., as determined by assays set forth in Section 5.3. infra.

In other embodiments, the present invention provides for analogs of CT-112 (SEQ. ID NO: 1) as anti-inflammatory agents in which any one or more of the amino acid residues of CT-112 (SEQ. ID NO: 1) are substituted by different amino acid analogs or mimics, e.g., to produce carbazates or tertiary centers, the incorporation of which serves to avoid or reduce proteolytic cleavage of the peptide, provided that said analogs exhibit anti-inflammatory activity, e.g., as determined by assays set forth in Section 5.3. infra.

In other embodiments, the present invention provides for truncated analogs of CT-112 (SEQ. ID NO: 1) as anti-inflammatory agents, provided that said truncated analogs exhibit anti-inflammatory activity, e.g., as determined by assays set forth in Section 5.3. infra.

In other embodiments, the present invention provides for substituted derivatives of CT-112 (SEQ. ID NO: 1) as anti-inflammatory agents, in which one or more amino acid residues of CT-112 (SEQ. ID NO: 1) are replaced by, e.g., the D-amino acid form of the particular amino acid residue, or by any different L-amino acid residue, provided that said substituted derivatives of CT-112 (SEQ. ID NO: 1) exhibit anti-inflammatory activity, e.g., as determined by assays set forth in Section 5.3. infra. For example, the present invention provides for a peptide having the amino acid sequence $Thr_1$-$Thr_2$-$Ser_3$-$Gln_4$-$Val_5$-$Arg_6$-$Pro_7$-$Arg_8$, wherein any one or more of the amino acid residues at positions 1, 2, 5, 6 or 7 is in the D-stereoisomeric form, and which peptide exhibits anti-inflammatory activity.

In addition, the present invention provides a peptide having the amino acid sequence Thr-Xaa-Ser-Gln-Val-Arg-Pro-Arg (SEQ ID NO 75), wherein Xaa is selected from the group consisting of nothing, L-Lys, L-Orn, L-Met, L-Arg, L-Ser, L-Trp, L-Tyr, L-Cys and L-His, and which peptide exhibits anti-inflammatory activity.

In addition, the present invention provides a peptide having the amino acid sequence Thr-Thr-Xaa-Gln-Val-Arg-Pro-Arg (SEQ ID NO 76), wherein Xaa is selected from the group consisting of nothing, L-Glu, L-Asp, L-Asn, L-Gln, L-Cys, L-His, L-Lys, L-Orn, L-Thr, L-Trp and L-Tyr, and which peptide exhibits anti-inflammatory activity.

In addition, the present invention provides a peptide having the amino acid sequence Thr-Thr-Ser-Xaa-Val-Arg-Pro-Arg (SEQ ID NO 77), wherein Xaa is selected from the group consisting of nothing, L-Lys, L-Orn, L-Arg, L-Asp, L-Cys, L-Glu., L-His, L-Met, L-Ser, L-Thr and L-Tyr, and which peptide exhibits anti-inflammatory activity.

In addition, the present invention provides a peptide having the amino acid sequence Thr-Thr-Ser-Gln-Xaa-Arg-Pro-Arg (SEQ ID NO 78), wherein Xaa is selected from the group consisting of nothing and all naturally occurring L-amino acids except Val, and preferably L-Lys, and which peptide exhibits anti-inflammatory activity.

In addition, the present invention provides a peptide having the amino acid sequence Thr-Thr-Ser-Gln-Val-Xaa-Pro-Arg (SEQ ID NO 79), wherein Xaa is selected from the group consisting of nothing and all naturally occurring L-amino acids except Arg, and preferably L-Ala or L-Glu, and which peptide exhibits anti-inflammatory activity.

In addition, the present invention provides a peptide having the amino acid sequence Thr-Thr-Ser-Gln-Val-Arg-Xaa-Arg (SEQ ID NO 80), wherein Xaa is selected from the group consisting of nothing and all naturally occurring L-amino acids except Pro, and which peptide exhibits anti-inflammatory activity.

In addition, the present invention provides a peptide having the amino acid sequence Thr-Thr-Ser-Gln-Val-Arg-Pro-Xaa (SEQ ID NO 81), wherein Xaa is selected from the group consisting of nothing, L-Lys, L-Orn, L-Asn, L-Asp, L-Cys, L-Glu, L-His, L-Met, L-Ser and L-Tyr, and which peptide exhibits anti-inflammatory activity.

In other embodiments, the present invention provides for analogs of CT-112 (SEQ. ID NO: 1) as anti-inflammatory agents in which one or more of the amino acid residues of CT-112 (SEQ. ID NO: 1) are omitted, provided that said analogs of CT-112 (SEQ. ID NO: 1) exhibit anti-inflammatory activity, e.g., as determined by assays set forth in Section 5.3. infra.

In other embodiments, the present invention provides for a peptide having the amino acid sequence R-$Xaa_1$-$Xaa_2$-$Xaa_3$-$Xaa_4$-$Xaa_5$-$Xaa_6$-$Xaa_7$-$Xaa_8$-R" (SEQ ID NO 74), wherein: R is either H or R'—(C=O)—, where R' is selected from the group consisting of a lower alkyl, a cycloalkyl, an aryl and a heteroaryl, wherein the aryl or heteroaryl is either unsubstituted or substituted with a halogen, methoxy, amino or alkyl functional group; R" is selected from the group consisting of OH, an amide, a lower alkyl ester, a cycloalkyl ester, an aryl ester and a heteroaryl ester, wherein the aryl ester or heteroaryl ester is either unsubstituted or substituted with a halogen, methoxy, amino or alkyl functional group; $Xaa_1$ is nothing or L-Thr; $Xaa_2$ is selected from the group consisting of nothing, L-Thr, L-Lys, L-Orn, L-Met, L-Arg, L-Ser, L-Trp, L-Tyr, L-Cys and L-His; $Xaa_3$ is selected from the group consisting of nothing, L-Ser, L-Glu, L-Asp, L-Asn, L-Gln, L-Cys, L-His, L-Lys, L-Orn; L-Thr, L-Trp and L-Tyr; $Xaa_4$ is selected from the group consisting of nothing, L-Gln, L-Lys, L-Orn; L-Arg, L-Asp, L-Cys, L-Glu, L-His, L-Met, L-Ser, L-Thr and L-Tyr; $Xaa_5$, $Xaa_6$ and $Xaa_7$ are each either nothing or any naturally occurring L-amino acids; and $Xaa_8$ is selected from the group consisting of nothing, L-Arg, L-Lys, L-Orn; L-Asn, L-Asp, L-Cys, L-Glu, L-His, L-Met, L-Ser and L-Tyr; provided that R-$Xaa_1$-$Xaa_2$-$Xaa_3$-$Xaa_4$-$Xaa_5$-$Xaa_6$-$Xaa_7$-$Xaa_8$R" (SEQ ID NO 74) comprises at least 4 amino acid residues, and is not Val-Arg-Pro-Arg (SEQ. ID NO: 4), or Thr-Thr-Ser-Gln-Val (SEQ. ID NO: 6), or Ser-Gln-Val-Arg-Pro-Arg (SEQ. ID NO: 3), or Thr-Thr-Ser-Gln-Val-Arg-Pro-Arg (SEQ. ID NO: 1); wherein the peptide may be derivatized or in which analogs may be synthesized from the peptide as described supra; and which peptide, peptide derivative or peptide analog exhibits anti-inflammatory activity, e.g., as determined by assays set forth in Section 5.3. infra.

In all cases, the peptides of the invention exhibit anti-inflammatory activity as defined in Section 5.3 infra.

The peptides of the invention may be prepared by any method known in the art. For example, and not by way of limitation, the peptides may be synthesized: (i) by cleavage from a larger peptide, such as, but not limited to, PF4 (SEQ. ID NO: 9); (ii) by recombinant DNA expression methods; and (iii) by chemical synthesis, including solid phase techniques as described by Barany and Merrifield (1980, in "The Peptides" Vol. 2, Gross and Meienhofer, eds., Academic Press, N.Y.).

In a preferred specific embodiment of the invention, tryptic digestion of PF4 (SEQ. ID NO: 9) may be performed to produce PF4 peptide fragments. For example, lyophilized PF4 (SEQ. ID NO: 9), prepared as described in Section 5.1, may be dissolved in 50 μl of 0.4 M $Na_2CO_3$/8M urea at pH=9 in a microcentrifuge tube. The protein may then be reduced by the addition of about 45 mM dithiothreitol in buffer at pH=8 for about 15 min at 50° C. The protein may then be carboxymethylated by addition of 5 μl of iodoacetic acid in 0.5N NaOH and incubated for about 15 min in the dark at room temperature. About 140 μl of deionized water and 5 μl of a 1 mM HCl solution of sequencer grade trypsin (at 200 μg/ml) may then be added and the sample incubated at 37° C. for about 24 hrs. The resulting tryptic digest may then be injected into an appropriate reverse phase chromatography column, e.g., a Vydac C18 column equilibrated with 2.7% acetonitrile/0.1% TFA/$H_2O$ and may be chromatographed at an appropriate flow rate, e.g., 0.5 ml/min with 1.0 min fractions collected. The elution program may be, e.g., 2.7% buffer B (95% acetonitrile) in buffer A (0.1% TEA in water) for about 10 min, and a gradient of about 27–95% buffer B in 123 min. Elution of the peptides may be monitored spectrophotometrically at a wavelength of 210 nm. Preferably, a Beckman System Gold HPLC System may be used for chromatography of both proteins and digests. Using the chromatography protocol set forth as an example supra, the CT-112 peptide (SEQ. ID NO: 1) may be expected to elute as peptide number 4 (see Section 6.2., infra). Peptide fragments of PF4 (SEQ. ID NO: 9) may, according to the invention, be optionally chemically modified, and may be tested for anti-inflammatory activity as set forth in the next section.

5.3. Identification of Anti-Inflammatory Peptides

Peptides as described supra may be determined to have anti-inflammatory activity using any in vitro or in vivo assay system known in the art to evaluate a factor for anti-inflammatory activity. The term "anti-inflammatory activity" should be construed herein to refer to an ability to inhibit inflammatory cell influx and/or activities associated with the activation of immune cells or the immune response. Thus, the term "anti-inflammatory" is intended to encompass an ability to act as an immuno-regulatory or immuno-modulatory agent.

For example, but not by way of limitation, the peptide may be tested for ability to inhibit inflammation in the mouse ear model in which arachidonic acid (AA) is used to induce an inflammatory reaction (Young et al., 1984, J. Invest. Dermatol. 82:367–371; Doherty et al., 1988, J. Invest. Dermatol. 91:298–302). For illustrative purposes, see Section 7, infra.

5.4. The Use of Peptides of the Invention as Anti-Inflammatory Agents

Peptides of the invention may be used in a method to inhibit inflammation in a tissue of a subject in need of such treatment who suffers from any disease or disorder in which either acute or chronic inflammatory cell influx occurs. The subject may be a human or non-human subject. Specific conditions in which peptides of the invention may have therapeutic value would include situations in which undesirable immune response has occurred, including, but not limited to, autoimmune diseases such as insulin-dependent diabetes, Goodpasture's syndrome, pemphigus and pemphigoid, primary biliary cirrhosis, ulcerative colitis, rheumatoid arthritis, scleroderma, mixed connective tissue disease and lupus erythematosus; graft versus host disease; septic shock; reperfusion injury (including injury subsequent to myocardial or cerebral infarction); atherosclerosis; asthma and inflammatory lung disease. In preferred specific embodiments of the invention, the peptide used to inhibit inflammation is CT-112 (Thr-Thr-Ser-Gln-Val-Arg-Pro-Arg) (SEQ. ID NO: 1).

The peptides of the invention may be administered by any suitable and accepted route of drug administration, including intravenous, subcutaneous, intradermal, intranasal, inhalation (e.q., by lung aerosol or lavage), intramuscular, intraocular, intraperitoneal injection, peritoneal lavage, cardiac puncture, cardiac catheter injection, oral, intrathecal or intraventricular injection, spinal column or cranial cavity injection, vaginal or rectal (e.g., by suppository), dermal patch or topical ointment, and may be comprised in any suitable pharmaceutical carrier, including aqueous solution, microcapsules, liposomes, or via a sustained-released implant, including hydrophilic or hydrophobic carrier-based implants.

The peptides of the invention may be administered at a dose which is effective in inhibiting inflammation in the subject as determined using standard techniques. "Inhibiting inflammation" should be construed to refer to a significant decrease in the signs and symptoms of inflammation. For example, but not by way of limitation, symptomatic relief, in which a patient is rendered subjectively relieved of discomfort, would be considered as one, among the many, satisfactory results of therapy. In certain specific non-limiting embodiments, the amount of inflammation may be decreased by about 50%; the $ED_{50}$ has been estimated to be a dose between about 2.5 and 5.0 mg/kg. In specific embodiments of the invention, CT-112 (SEQ. ID NO: 1) may be administered to a human patient at a dose of about 2.5 mg/kg to about 500 mg/kg. In preferred, specific, non-limiting embodiments of the invention, the dose, administered subcutaneously to a human patient, may be either about 5 mg/kg, 50 mg/kg, or 100 mg/kg, depending upon whether the inflammation to be treated is mild, moderate, or severe/persistent. The dose may be administered at appropriate intervals, e.g., but not limited to, daily, or once, twice, or three times a week.

6. EXAMPLE: PREPARATION OF ANTI-INFLAMMATORY PEPTIDES

6.1. Materials and Methods

6.1.1. Preparation of PF4

PF4 (SEQ. ID NO: 9) was purified from thrombin-activated platelet extracts by a modification of the method described by Medici et al. (1989, Thrombos. Res. 54:277–287). PF4 (SEQ. ID NO: 9) was isolated by heparin sepharose affinity chromatography with elution of the factor at 1.7M NaCl, followed by strong ion exchange chromatography on a polysulfoethyl-aspartamide column eluted with NaCl in the presence of 15% acetonitrile and finally by separation on a Vydac $RPC_4$ reverse-phase HPLC analytical column eluted with a linear acetonitrile gradient in 0.1% TFA in water.

6.1.2. Tryptic Digestion of PF4

Tryptic digestion was performed by dissolving lyophilized PF4 (SEQ. ID NO: 9) in 50 μl of 0.4M $Na_2CO_3$/8M urea pH 9.0 in a microcentrifuge tube. The protein was then reduced by addition of 5 μl of 45 mM DTT in pH 9.0 buffer for 15 min at 50° C. The protein was carboxymethylated by addition of 5 μl of iodoacetic acid in 0.5N NaOH and incubated for 15 min in the dark at room temperature. Finally, 140 μl of deionized water and 5 μl of 1 mM HCl solution of sequencer grade trypsin (200 μg/ml) was added and the sample incubated for 24 hrs at 37° C.

The tryptic digest was injected onto a Vydac $C_{18}$ column equilibrated with 2.7% Acetonitrile/0.1% TFA/$H_2O$ and was chromatographed at a flow rate of 0.5 ml/min with 1.0 min fractions collected. The elution pattern was as follows: 2.7% buffer B (95% acetonitrile) in buffer A (0.1% TFA in water) for 10 min, 2.7% to 95% buffer B in 123 min. The elution of the peptides was monitored at 210 nm. A Beckman System Gold HPLC System was used for chromatography of both proteins and digests.

6.2. Results and Discussion

CT-112 (SEQ. ID NO: 1) eluted as the fourth peptide in reverse phase HPLC, and was sequenced in a Porton 2090e sequencer after adsorption onto a Porton proprietary peptide support. The sequence of the peptide was: Thr-27.5pm, Thr-23.5pm, Ser-30.0pm, Gln-26.5pm, Val-22.6pm, Arg-10.5pm, Pro-9.2pm, Arg-4.7pm. Amino acid analysis using the Beckman Dabsyl Chloride method confirmed the total sequence of the peptide.

7. EXAMPLE: CT-112 EXHIBITS ANTI-INFLAMMATORY ACTIVITY

7.1. Materials and Methods

The anti-inflammatory properties of CT-112 (SEQ. ID NO: 1) were assessed using a standardized assay for antiinflammatory activity, i.e., the mouse ear model in which arachidonic acid (AA) is used to induce an inflammatory reaction (Young et al., 1984, J. Invest. Dermatol. 82:367–371; Doherty, et al., 1988, J. Invest. Dermatol. 91:298–302).

7.1.1. Reagents

CT-112 (SEQ. ID NO: 1), either the chloride salt or the trifluoroacetic acid salt, was synthesized using a standard organic synthesis scheme for peptides by Multiple Peptide Systems (San Diego, Calif. USA). Phenidone and AA were obtained from Sigma Chemical Co. (St. Louis, Mo. USA). Alzet minipumps (Model 2001, 7-day, set to deliver 1 µl/hr), to be implanted subcutaneously in test animals, were obtained from Alza Corporation (Palo Alto, Calif. USA). AA was dissolved in reagent-grade acetone at 200 mg/ml prior to application.

7.1.2. Animal Treatment

Female mice (C57BL/6UAF, Charles River Breeding Laboratories, approximately 15–18 g) were obtained and acclimated for 2 weeks prior to use. The animals were approximately 14 weeks old at the start of the study.

To prepare minipumps for implantation, CT-112 (SEQ. ID NO: 1) was dissolved in PBS. The material was loaded into Alzet minipumps set to deliver 0.05 (5 animals), 0.1 (10 animals), 1 (10 animals), or 2.5 (5 animals) mg of CT-112 (SEQ. ID NO: 1) per animal per day. Minipumps for implantation into control animals contained only PBS. As a positive control, one set of 10 mice received 100 mg/kg of phenidone, a potent 5-lipoxygenase inhibitor which acts as an anti-inflammatory agent, 15 min prior to challenge with AA.

For subcutaneous implantation of minipumps, animals were anesthetized with Ketamine/Xylazine. The Ketamine (Aveco Lot #440140) was injected at 80 mg/kg and the Xylazine (Rugby Laboratories Lot #26040-B) at 16 mg/kg and the Alzet pumps were implanted subcutaneously in the dorsothoracic area. Animals were allowed to recover and then housed and given food and water ad libitum for 5 days.

On the sixth day following pump implantation, 0.01 ml of AA was applied to the inner and outer surfaces of the right ear by means of an automatic microliter pipette. One hr following AA application, the mice were sacrificed and ear thickness was measured with a Mitutoyo No. 7300 Gauge Caliper. The left ears were also measured as an internal control.

Myeloperoxidase activity in ear tissue was measured as a marker for the presence or absence of polymorphonuclear leukocytes (PMNs) (Barone et al., 1991, J. Neurosci. Res. 29:336–345). After measurement of ear thickness, ears were dissected from the mice and homogenized in 50 mM Tris-HCL, pH 7.4 at 4° C. to give a 10% (w/v) homogenate. Aliquots of the homogenate were used to determine the amount of myeloperoxidase activity present in the tissue using o-dianisidine (Sigma Chem Co., St. Louis Mo.) and hydrogen peroxide as substrates and monitoring chromophore generation at 460 nm (Barone et al., 1991, J. Neurosci. Res. 29:336–345).

7.2. Results and Discussion

Pretreatment of animals with the 5-lipoxygenase inhibitor phenidone effectively prevented the inflammatory response to topical AA application. This non-steroidal, anti-inflammatory agent was thus able to serve as a positive control for inhibition of AA-induced dermal inflammation in this study.

Pretreatment of mice with CT-112 (SEQ. ID NO: 1) significantly inhibited the inflammation process compared to PBS controls. Pretreatment of mice with 0.05 mg of CT-112 (SEQ. ID NO: 1) per day resulted in a significant reduction (43.1%, $p \leq 0.05$) in ear swelling in response to AA (Table I). Maximum reduction (95.6%) of the response to AA was achieved when 2.5 mg of CT-112 (SEQ. ID NO: 1) were administered per day to each animal. This inhibition of the inflammatory response was significant ($p \leq 0.01$) and was comparable to the response to phenidone.

Pretreatment of mice with 0.05–1 mg of CT-112 (SEQ. ID NO: 1) per day decreased the myeloperoxidase activity in the AA treated ears in a dose dependent manner. Due to the large variability in the test only the group which received either phenidone or 0.1 mg/day of CT-112 (SEQ. ID NO: 1) demonstrated a significantly different level ($p<0.05$) of activity when compared to control myeloperoxidase activity (Table II).

These data indicate that CT-112 (SEQ. ID NO: 1) can inhibit an acute dermal inflammatory response due to the topical administration of AA. This effect may also result in the presence of fewer PMNs in the inflammatory response as determined by myeloperoxidase activity.

TABLE I

Effect of CT-112 on Arachidonic Acid Induced Inflammation

| Treatment | Ear Thickness (in) | | % Reduction of Ear Swelling |
|---|---|---|---|
| Control (PBS) | 0.01999 ± 0.00452 | (5) | 0.0% |
| Phenidone (100 mg/kg) | 0.01176 ± 0.00080 | (10)** | 84.1% |
| CT-112 (0.05 mg/animal/day) | 0.01577 ± 0.00155 | (5)* | 43.1% |
| CT-112 (0.1 mg/animal/day) | 0.01577 ± 0.00191 | (10)** | 43.1% |
| CT-112 (1.0 mg/animal/day) | 0.01128 ± 0.00291 | (10)** | 89.0% |
| CT-112 (2.5 mg/animal/day) | 0.01060 ± 0.00175 | (5)** | 95.6% |
| Control ear (no arachidonic acid) | 0.01020 ± 0.00272 | (50)** | — |

Values represent the mean ± SD of the number of ears in parentheses.
*Indicates significantly different from the control PBS-treated group at $P \leq 0.05$ using Student's t-test.
**Indicates significantly different from the control treated group at $p \leq 0.01$ using Student's t-test.

TABLE II

Effect of CT-112 on Arachidonic Acid Induced Myeloperoxidase Activity in Mouse Ear

| Treatment | Myeloperoxidase Activity (µmole of chromophore formed/min) | |
|---|---|---|
| Control (PBS) | 28.0 ± 5.8 | (4) |
| Phenidone (100 mg/animal/day) | 14.5 ± 8.6 | (5)* |
| CT-112 (0.05 mg/animal/day) | 19.6 ± 15.6 | (5) |
| CT-112 (0.1 mg/animal/day) | 17.0 ± 9.6 | (5)* |
| CT-112 (1.0 mg/animal/day) | 14.7 ± 13.3 | (5) |

Values represent the mean ± SD of the number of ears in parentheses.
*Indicates significantly different from the control PBS group at $p \leq 0.05$ using the Mann Whitney test.

8. EXAMPLE: CT-112 INHIBITION OF NEUTROPHIL CHEMOTAXIS

The ability of CT-112 (SEQ. ID NO: 1) to block specific inflammatory processes is demonstrated by its inhibition of neutrophil activity, which has been examined as described below.

8.1. Materials and Methods

The ability of CT-112 (SEQ. ID NO: 1) to inhibit chemotaxis of neutrophils in response to a variety of agents was assessed using Neuroprobe chemotaxis chambers. For these assays, neutrophils were resuspended in Hank's balanced salt solution with $Ca^{2+}$ and $Mg^{2+}$ to give a $5 \times 10^6$ cells/ml suspension after the cells were labeled with 1',7'-bis(2-carboxyethyl)-5-(6)-carboxyfluorescein. The neutrophils were exposed to CT-112 (SEQ. ID NO: 1) for approximately 15 min prior to addition to the chemotaxis chambers. CT-112 (SEQ. ID NO: 1) was present in both the top and bottom of the chambers, and the chemoattractant, either f-Met-Leu-Phe, leukotriene $B_4$ or interleukin-8, was added to the bottom of chamber. Cells which had migrated through the membrane were determined by fluorescence at 530 nm at 1 hr after initiation of the assay.

8.2. Results and Discussion

CT-112 (SEQ. ID NO: 1) effectively inhibited the chemotactic migration of neutrophils to both f-Met-Leu-Phe and $LTB_4$ (FIGS. 3, 4), but not to interleukin-8 (FIG. 5). In addition, CT-112 (SEQ. ID NO: 1) was not cytotoxic to neutrophils, as determined by viability testing using trypan blue exclusion (FIG. 3). This study indicates that at least one activity associated with neutrophils, that of chemotactic migration, is at least: partially inhibited by CT-112 (SEQ. ID NO: 1).

9. EXAMPLE: EFFECT OF DURATION OF EXPOSURE TO CT-112

9.1. Materials and Methods

Mice were implanted with Alzet mini-pumps set to deliver 60 mg/kg/day for either 7, 3, or 1 days. A separate group of 5 mice received 3 intraperitoneal injections of CT-112 (60 mg/kg/injection) at 24, 1 and 0.25 hr prior to AA challenge. CT-112 (SEQ. ID NO: 1) was prepared for injection by dissolving the compound in Dulbecco's PBS to give a final CT-112 (SEQ. ID NO: 1) concentration of 5 mg/ml. The control mice were implanted with Alzet minipumps that delivered PBS for 7 days. The AA challenge was the same as described supra in Example 7.

9.2. Results and Discussion

The results are presented in Table III. No difference in the inhibition of inflammation was detected as a result of the 7, 3 and 1 day exposures. All durations significantly inhibited ($p \leq 0.05$) the acute inflammation otherwise induced by the topical application of AA. The intraperitoneal injections inhibited inflammation although the results were not significantly different from the control. These results indicate that prolonged exposure to CT-112 (SEQ. ID NO: 1), i.e., >1 day, was not necessary to inhibit inflammation.

TABLE III

Effect of Duration of Exposure on the Activity of CT-112

| Treatment Group | Thickness Difference (Left-Right) (in) | % Inhibition of Inflammation |
| --- | --- | --- |
| Control (PBS) | 0.00594 ± 0.00342 | 0 |
| Phenidone (100 mg/kg) | 0.00073 ± 0.00153* | 88 |
| 7-day pump | −0.00051 ± 0.00116* | 108 |
| 3-day pump | −0.00115 ± 0.00058* | 119 |

TABLE III-continued

Effect of Duration of Exposure on the Activity of CT-112

| Treatment Group | Thickness Difference (Left-Right) (in) | % Inhibition of Inflammation |
| --- | --- | --- |
| 1-day pump | −0.00074 ± 0.00119* | 112 |
| −24, 1, 0.25 hr, ip | 0.00226 ± 0.00124 | 62 |

Values represent the mean ± SD of 5 animals.
*Indicates significantly different from PBS-treated animals at $p \leq 0.05$.

10. EXAMPLE: EFFECT OF INTRAPERITONEAL INJECTION OF CT-112

10.1. Materials and Methods

Administration of CT-112 (SEQ. ID NO: 1) (60 mg/kg/injection) via multiple intraperitoneal injections was performed at the following times prior to AA challenge:

a) 6, 3, 1 and 0.25 hr;
b) 3, 1 and 0.25 hr; or
c) 1 and 0.25 hr.

In addition, the effect of a single administration of CT-112 (SEQ. ID NO: 1) (60 mg/kg) by intraperitoneal injection was performed at either 1 or 3 hr prior to AA challenge. Control mice had Alzet minipumps implanted to deliver PBS for 7 days prior to AA challenge. The AA challenge was the same as described supra in Example 7. The results of the multiple dosing regimens and the 1 hr and 3 hr single dosing regimens were compared to the anti-inflammatory activity of CT-112 (SEQ. ID NO: 1) delivered via Alzet minipump set to deliver 60 mg/kg/day for 7 days using 5 animals per treatment.

In a separate experiment, the effect of multiple intraperitoneal injections of CT-112 (SEQ. ID NO: 1) at either 6, 3, 1 and 0.25 hr, or 16, 3, 1 and 0.25 hr prior to AA challenge was assessed. The results of both multi-dosing regimens were compared to both phenidone (100 mg/kg administered 15 min prior to AA challenge) and CT-112 (SEQ. ID NO: 1) administered via Alzet mini-pump (60 mg/kg/day for 7 days). For this latter study, the number of animals receiving the single injection of CT-112 (SEQ. ID NO: 1) was increased from 5 to 10.

10.2. Results and Discussion

The results of the multiple and single (1 hr and 3 hr) dosing studies are presented in Table IV. All multi-dosing regimens and the 3 hr single dosing regimen significantly inhibited ($p \leq 0.01$) the inflammatory process approximately 70% as compared to the 7-day administration with the Alzet mini-pump which inhibited the inflammatory process by 94%. Although the single dose of CT-112 (SEQ. ID NO: 1) administered 1 hr prior to AA challenge did not significantly inhibit the inflammatory process, a 43% inhibition was observed.

Administration of multiple IP) injections of CT-112 (SEQ. ID NO: 1), at either 6, 3, 1 and 0.25 hr or 16, 3, 1 and 0.25 hr prior to AA challenge, resulted in a significant reduction (56–61%) ($p \leq 0.01$) in inflammation (Table V). However, both the 7-day Alzet mini-pump administration of CT-112 (SEQ. ID NO: 1) and the single administration of phenidone 15 min prior to AA challenge resulted in a greater reduction in inflammation.

These results indicate that CT-112 (SEQ. ID NO: 1) given via intraperitoneal injection can significantly inhibit acute dermal inflammation.

TABLE IV

Effect of Intraperitoneal Administration of CT-112 on Activity

| Treatment Group | Thickness Difference (Left-Right) (in) | % Inhibition of Inflammation |
|---|---|---|
| Control (PBS) | 0.00539 ± 0.00173 | 0.0 |
| 7-day pump | 0.00033 ± 0.00065** | 93.9 |
| −6,3,1,.25 hr ip | 0.00144 ± 0.00126** | 73.2 |
| −3,1,.25 hr ip | 0.00141 ± 0.00138** | 73.8 |
| −1,.25 hr ip | 0.00192 ± 0.00148** | 64.4 |
| −3 hr ip | 0.00116 ± 0.00100** | 78.5 |
| −1 hr ip | 0.00308 ± 0.00189 | 42.9 |

Values represent the mean ± SD of 5 animals.
**Indicates significantly different from PBS-treated animals at $p \leq -0.01$.

TABLE V

Effect of a Intraperitoneal Administration of CT-112 on Activity

| Treatment Group | Thickness Difference (Left-Right) (in) | % Inhibition of Inflammation |
|---|---|---|
| Control (PBS) | 0.00647 ± 0.00170(5) | 0.0 |
| Phenidone (100 mg/kg) | 0.00102 ± 0.00038(5)** | 84.2 |
| 7-day pump | −0.00003 ± 0.00120(5)** | 100.5 |
| −6,3,1,0.25 hr ip | 0.00249 ± 0.00170(10)** | 61.4 |
| −16,3,1,0.25 hr ip | 0.00283 ± 0.00218(10)** | 56.3 |

Values represent the mean ± SD of the number of animals indicated in parentheses.
**Indicates significantly different from PBS-treated animals at $p \leq 0.01$.

11. EXAMPLE: EFFECT OF SUBCUTANEOUS INJECTION OF CT-112

This example demonstrates that CT-112 (SEQ. ID NO: 1) administered via subcutaneous injection is effective in inhibiting an inflammatory response.

11.1. Materials and Methods

Administration to mice of CT-112 (SEQ. ID NO: 1) (60 mg/kg/injection) via multiple subcutaneous injections prior to AA challenge was performed at:

a) 6, 3, 1 and 0.25 hr;

b) 3, 1 and 0.25 hr; or c) 1 and 0.25 hr.

In addition, other mice received only a single subcutaneous injection of CT-112 (SEQ. ID NO: 1) (60 mg/kg) at either 3 or 1 hr prior to AA challenge. Control animals were implanted 3 days prior to AA challenge with Alzet minipumps filled with PBS. The AA challenge was the same as described supra in Example 7. The results of these dosing regimens were compared to the anti-inflammatory activity of CT-112 (SEQ. ID NO: 1) delivered via Alzet minipump set to deliver 60 mg/kg/day for 7 days. The duration of activity of CT-112 (SEQ. ID NO: 1) with respect to acute anti-inflammatory activity was also assessed following subcutaneous injection of CT-112 (SEQ. ID NO: 1).

11.2. Results and Discussion

The results are presented in Tables VI and VII.

For subcutaneous injection, all multi-dosing regimens and single-dosing regimens significantly inhibited ($p \leq 0.05$) the inflammatory process by approximately 70% as compared to the 7-day administration with the Alzet minipump which inhibited the inflammatory process by 87% (Table VI).

In the duration study, although only treatment with CT-112 (SEQ. ID NO: 1) administered subcutaneously 6 hr prior to AA challenge significantly inhibited ($p \leq 0.05$) the AA-induced acute inflammation (Table VII), the results suggest that the duration of activity is greater than 6 hr. In this particular study, administration of 60 mg/kg/day of CT-112 (SEQ. ID NO: 1) via Alzet mini-pump failed to achieve the normally observed 80–90% inhibition of inflammation. These results indicate that CT-112 (SEQ. ID NO: 1) was active at inhibiting acute dermal inflammation when administered via subcutaneous injection 6 hr prior to challenge.

TABLE VI

Effect of Subcutaneous Administration of CT-112 on Activity

| Treatment Group | Thickness Difference (Left-Right) (in) | % Inhibition of Inflammation |
|---|---|---|
| Control (PBS) | 0.00617 ± 0.00315 | 0.0 |
| 7-day pump | 0.00083 ± 0.00084** | 86.5 |
| −6,3,1,.25 hr, sc | 0.00147 ± 0.00041* | 76.2 |
| −3,1,.25 hr, sc | 0.00193 ± 0.00070* | 68.7 |
| −1,.25 hr, sc | 0.00195 ± 0.00131* | 68.4 |
| −3 hr, sc | 0.00213 ± 0.00089* | 65.5 |
| −1 hr sc | 0.00174 ± 0.00128* | 71.8 |

Values represent the mean ± SD of 5 animals.
*Indicates significantly different from PBS-treated animals at $p \leq 0.05$.
**Indicates significantly different from PBS-treated animals at $p \leq 0.01$.

TABLE VII

Effect of a Single Subcutaneous Administration of CT-112 on Activity

| Treatment Group | Thickness Difference (Left-Right) (in) | % Inhibition of Inflammation |
|---|---|---|
| Control | 0.00385 ± 0.00187 | 0.0 |
| 3 day pump | 0.00127 ± 0.00128* | 67.0 |
| −3 hr, ip | 0.00242 ± 0.00187 | 37.2 |
| −6 hr, sc | 0.00117 ± 0.00066* | 69.6 |
| −3 hr, sc | 0.00243 ± 0.00107 | 36.9 |
| −1 hr, sc | 0.00214 ± 0.00122 | 44.5 |
| −.25 sc | 0.00252 ± 0.00128 | 34.7 |

Values represent the mean ± SD of 5 animals.
*Indicates significantly different from PBS-treated animals at $p \leq 0.05$.

12. EXAMPLE: EFFECT OF ORAL ADMINISTRATION OF CT-112

12.1. Materials and Methods

The ability of orally delivered CT-112 (SEQ. ID NO: 1) to effectively inhibit inflammation has been assessed in mice.

Administration of CT-112 (SEQ. ID NO: 1) (200 mg/kg/gavage) via multiple gavages was performed at the following times prior to AA challenge:

a) 6, 3, 1 and 0.25 hr;

b) 3, 1 and 0.25 hr; or c) 1 and 0.25 hr.

In addition, the effect of a single gavage of CT-112 (SEQ. ID NO: 1) (200 mg/kg) administered at either 3 or 1 hr prior to AA challenge was assessed. The AA challenge was the same as described supra in Example 7. The results of these multi- or single-dosing regimens were compared to the anti-inflammatory activity of CT-112 (SEQ. ID NO: 1) delivered via Alzet minipump set to deliver 60 mg/kg/day for 3 days.

12.2. Results and Discussion

The results are presented in Table VIII. All orally administered, multi-dosing and single-dosing regimens significantly inhibited (52–94%) ($p \leq 0.01$ or $\leq 0.05$) the inflammatory process, with the exception of the dosing regimen in which CT-112 (SEQ. ID NO: 1) was administered at 3, 1, and 0.25 hr prior to AA challenge. This dosing regimen inhibited the inflammatory process by only 44% and failed to achieve statistical significance. In this study, the 3-day administration with the Alzet mini-pump inhibited the inflammatory process by 88%. These results indicate that CT-112 (SEQ. ID NO: 1) is active when administered orally to mice at least 1 hr prior to challenge as well as up to 3 hr prior to challenge.

TABLE VIII

| Treatment Group | Effect of Oral Administration of CT-112 on Activity | |
|---|---|---|
| | Thickness Difference (Left-Right) (in) | % Inhibition of Inflammation |
| Control (PBS) | 0.00501 ± 0.00188 | 0.0 |
| 3 day pump | 0.00058 ± 0.00086** | 88.4 |
| −6,3,1,.25 hr, po | 0.00134 ± 0.00257* | 73.3 |
| −3,1,.25 hr, po | 0.00280 ± 0.00114 | 44.1 |
| −1,.25 hr, po | 0.00241 ± 0.00124* | 51.9 |
| −3 hr, po | 0.00031 ± 0.00198** | 93.8 |
| −1 hr, po | 0.00139 ± 0.00122** | 72.3 |

Values represent the mean ± SD of 5 animals.
*Indicates significantly different from PBS-treated animals at $p \leq 0.05$.
**Indicates significantly different from PBS-treated animals at $p \leq 0.01$.

13. EXAMPLE: EFFECT OF CT-112 ON THE CARAGEENAN-INDUCED MODEL OF PERITONITIS

The ability of CT-112 (SEQ. ID NO: 1) to inhibit inflammation was further examined in the carrageenan-induced model of peritonitis. This model provides a more rigorous test of the ability of CT-112 (SEQ. ID NO: 1) to inhibit inflammation than the mouse ear AA-induced acute inflammation model (Hanna et al., 1990, Drugs Exp.Clin. Res. 16(4):137–178; Brown and Leslie, 1976, Surg. Gynecol. Obstet. 143:738–740).

13.1. Materials and Methods

Mice (C57BL/6UAF, females, 12 weeks old) were implanted with Alzet mini pumps set to deliver 60 mg CT-112/kg/day. Six days post-implantation, the mice were challenged with an intraperitoneal injection of 0.3 ml of carrageenan in PBS (10 mg/ml). The peritoneal cavity was lavaged with 15 ml of Hank's Balanced Salt Solution ($Ca^{2+}$- and $Mg^{2+}$-free) at 24, 48 and 72 hr post-challenge. The lavage fluid was centrifuged (500 g, 5 min), fixed with LeukoStat fixative and stained with LeukoStat staining solution. The slides were analyzed under a microscope for the different types of inflammatory cells, such as macrophages, lymphocytes and neutrophils. At the 48-hr time point, 5 control mice were also lavaged.

In a separate study, the peritoneal lavage fluid was analyzed for total leukotriene $B_4$ ($LTB_4$) and prostaglandin $E_2$ ($PGE_2$) content at 24 hr post-challenge (Griswold et al., 1991, Biochem. Pharmacol. 42(4):825–831).

13.2. Results and Discussion

The results are presented in Table IX and FIG. 6. CT-112 (SEQ. ID NO: 1) decreased neutrophil influx into the peritoneum in response to carrageenan injection. This decrease resulted in a reduction in the number of neutrophils in the peritoneum at 72 hr post-challenge that was statistically significant ($p \leq 0.05$). In this study, the number of macrophages appeared to increase in response to the administration of CT-112 (SEQ. ID NO: 1). No significant effect on lymphocytes was observed. These results indicate that CT-112 does not inhibit the recruitment of macrophages to a site of inflammation.

The results of the analysis of $LTB_4$ and $PGE_2$ are presented in Table X. After administration of CT-112 (SEQ. ID NO: 1), a statistically significant ($p \leq 0.05$) reduction in the amount of $PGE_2$ was noted in the peritoneal lavage fluid, while the amount of $LTB_4$ was not affected. These results indicate that at least one part of the AA metabolic pathway involved in inflammation is inhibited.

TABLE IX

| Effect of CT-112 on Inflammatory Cell Influx in a Model of Peritonitis | | | | |
|---|---|---|---|---|
| Time Post Carrageenan | Treatment | Absolute Cell Number | | |
| | | Lymphocytes | Neutrophils | Macrophages |
| Normal (none) | None | 18.4 ± 11.9 | 4.4 ± 5.2 | 21.6 ± 18.7 |
| 24 hr | Control | 15.7 ± 9.9 | 132 ± 32 | 17.1 ± 8 |
| | CT-112 | 16.9 ± 5.9 | 106 ± 29 | 19.5 ± 10 |
| 48 hr | Control | 14.1 ± 8.1 | 199 ± 48 | 72.7 ± 14 |
| | CT-112 | 12.5 ± 7.6 | 134 ± 77 | 126 ± 43* |
| 72 hr | Control | 21.0 ± 20 | 157.5 ± 93 | 229 ± 106 |
| | CT-112 | 45.1 ± 42 | 48.4 ± 28* | 255 ± 125 |

Values represent the mean ± SD of 5 animals.
*Indicates significantly different from the carrageenan-treated animals at the same time point at $p \leq 0.05$.

TABLE X

| Effect of CT-112 on Inflammatory Mediators in Peritonitis | | |
|---|---|---|
| | $LTB_4$ | $PGE_2$ |
| Treatment Group | (pg in peritoneal lavage) | |
| Control (PBS) | 15.8 ± 4.3(5) | 21.4 ± 3.8(5) |
| CT-112 (60 mg/kg/day) | 16.8 ± 11.5(5) | 13.1 ± 6.9(5)* |

Values represent the mean ± SD of 5 animals.
*Indicates significantly different from PBS-treated animals at $p \leq 0.05$.

14. EXAMPLE: STRUCTURE ACTIVITY RELATIONSHIPS

14.1. Comparison of Anti-Inflammatory Activities of CT-114 and CT-112

14.1.1. Materials and Methods

CT-114 (Thr-Thr-Ser-Gln-Val) (SEQ. ID NO: 6), which is an analog of CT-112 (SEQ. ID NO: 1), was separately tested as a potential secondary pharmacophore in the mouse ear acute inflammation model. In this study, CT-114 (SEQ. ID NO: 6) and CT-112 (SEQ. ID NO: 1) were each separately prepared and loaded into different Alzet minipumps set to deliver either 6 mg or 60 mg peptide/kg/day. Three days after implantation, mice were challenged by application of AA to the left ear. The AA challenge was the same as described supra in Example 7.

14.1.2. Results and Discussion

The results are presented in Table XI. Inflammation in mice treated with 6 mg/kg/24 hr of CT-112 (SEQ. ID NO: 1) was not statistically different from the control. The 6 mg/kg/day dose of CT-114 (SEQ. ID NO: 6) significantly inhibited ($p \leq 0.05$) the inflammatory process compared to the control, resulting in a statistically significant difference ($p \leq 0.05$) between the inhibition of inflammation caused by CT-112 (SEQ. ID NO: 1) and that caused by CT-114 (SEQ. ID NO: 6). Both CT-112 (SEQ. ID NO: 1) and CT-114 (SEQ. ID NO: 6) significantly inhibited ($p \leq 0.01$ and $p \leq 0.05$, respectively) the inflammatory process at 60 mg/kg/24 hr, and there was no statistical difference between these two groups. These results indicate that CT-112 (SEQ. ID NO: 1) and CT-114 (SEQ. ID NO: 6) are both capable of inhibiting acute dermal inflammation.

TABLE XI

| Treatment Group | Comparison of the Activity of CT-112 to CT-114 | |
|---|---|---|
| | Thickness Difference (Left-Right) (in) | % Inhibition of Inflammation |
| Control (PBS) | 0.00644 ± 0.00258 | 0.0 |
| CT-112 at 6 mg/kg | 0.00381 ± 0.00066 | 40.8 |
| CT-114 at 6 mg/kg | 0.00262 ± 0.00092*† | 59.3 |
| CT-112 at 60 mg/kg | 0.00095 ± 0.00064** | 85.2 |
| CT-114 at 60 mg/kg | 0.00242 ± 0.00074* | 62.4 |

Values represent the mean ± SD of 5 animals.
*Indicates significantly different from PBS-treated animals at $p \leq 0.05$.
**Indicates significantly different from PBS treated animals at $p \leq 0.01$.
†Indicates significantly different from CT-112 (6 mg/kg/day) treated animals at $p \leq 0.05$.

14.2. Anti-Inflammatory Activity of Other Peptides

Because CT-112 (SEQ. ID NO: 1) and CT-114 (SEQ. ID NO: 6) are peptides derived from PF4 (SEQ. ID NO: 9), which is a member of the α-chemokine family, and because both CT-112 (SEQ. ID NO: 1) and CT-114 (SEQ. ID NO: 6) are situated two amino acid residues toward the carboxyl-terminal end from the highly conserved CXC portion of α-chemokines (Edgington, 1993, Bio/Technology 11:676–678; Broxmeyer et al., 1993 J. Immunol. 150: 3448–3458), a series of peptides found at the same locus in other members of the α-chemokine family were synthesized and tested for anti-inflammatory activity in the mouse ear acute inflammation model.

In addition, a series of peptides derived from the same position (two amino acid residues toward the carboxyl terminal end of the CC motif) from the β-chemokine family were also tested (note: α-chemokines have activity specific for neutrophils and T-cells and β-chemokines have activity specific for macrophages and monocytes). A random octapeptide, CT-120 (Val-Thr-Arg-Pro-Thr-Gln-Arg-Ser) (SEQ. ID NO: 11), unrelated sequences from growth factors, and albumin were also tested.

14.2.1. Materials and Methods

Each peptide was administered for 24 hr via an Alzet pump set to deliver 60 mg/kg/day. Due to the large number of animals in this study, groups of compounds were randomly tested and compared to animals treated with either CT-112 (SEQ. ID NO: 1) or with PBS alone, and evaluated for their ability to inhibit inflammation. The AA challenge was the same as described supra in Example 7.

14.2.2. Results and Discussion

The results are presented in Tables XII through XV. Although no easily discernible pattern of activity was identified, the following results were observed. No compound was more effective than CT-112 (SEQ. ID NO: 1) in inhibiting AA-induced inflammation. The most effective compounds (other than CT-112) were CT-119 (SEQ. ID NO: 21), CT-164 (SEQ. ID NO: 16) and CT-220 (SEQ. ID NO: 23). Of these compounds, only CT-164 is derived from the α-chemokine family (hENA78). A random sequence of amino acid residues, CT-120 (SEQ. ID NO: 11), was ineffective in inhibition of the AA-induced ear inflammation. Although albumin produced a modest inhibition of inflammation, this phenomenon has been observed by others and is not considered biologically significant. These results indicate that a number of peptides derived from the sequences found in both α- and β-chemokines may inhibit acute dermal inflammation. However, of the sequences tested, none were more effective than CT-112 (SEQ. ID NO: 1).

TABLE XII

| Comparison of Anti-inflammatory Activity of Peptides to CT-112 | | | | |
|---|---|---|---|---|
| Compound | Derived From | SEQ. ID. NO. | Amino Acid Sequence | % INHIBITION |
| α-Chemokines | | | | |
| CT-112 | PF4 | 1 | Cys Leu Cys Val Lys Thr Thr Ser Gln Val Arg Pro Arg | 78 |
| CT-127 | CTAPIII | 12 | Cys Met Cys Ile Lys Thr Thr Ser Gly Ile His Pro Lys | 41 |
| CT-123 | IL-8 | 13 | Cys Gln Cys Ile Lys Thr Tyr Ser Lys Pro Phe His Lys | 65 |
| CT-176 | GRO-α | 14 | Cys Gln Cys Leu Gln Thr Leu Gln Gly Ile His Pro Lys | 67 |
| CT-173 | NAP-4 | 15 | Cys Leu Cys Asp Leu Gln Val Lys Thr Val Lys Gln Val Ser | 58 |
| CT-164 | hENA78 | 16 | Cys Val Cys Leu Gln Thr Thr Gln Gly Val His Pro Lys | 76 |
| β-Chemokines | | | | |
| CT-201 | RANTESβ | 17 | Cys Cys Phe Ala Tyr Ile Ala Arg Pro Leu Pro Arg | 48 |
| CT-183 | hACT2β | 18 | Cys Cys Phe Ser Tyr Thr Ala Arg Lys Leu Pro Arg Asn Phe | 51 |
| CT-144 | HMIP1bβ | 19 | Cys Cys Phe Ser Tyr Thr Arg Glu Ala Ser Ser Asn Phe | 51 |

TABLE XII-continued

Comparison of Anti-inflammatory Activity of Peptides to CT-112

| Compound | Derived From | SEQ. ID. NO. | Amino Acid Sequence | % INHIBITION |
|---|---|---|---|---|
| CT-135 | PECAM | 20 | Thr Thr Ser His Val Lys Pro Gln | 73 |
| CT-119 | TNF-α | 21 | Thr His Val Leu Leu Thr His Thr Ile | 74 |
| CT-125 | PDGF-B | 22 | Val Gln Val Arg Lys Ile Glu Ile Val Arg Lys Lys Pro Ile | 56 |
| CT-220 | PDGF-A | 23 | Thr Thr Ser Leu Asn Pro Asp Tyr Arg | 73 |
| CT-120 | RANDOM | 11 | Val Thr Arg Pro Thr Gln Arg Ser | 32 |
| CT-XXX | ALBUMIN | | | 47 |

Underlined sequences represent the compound tested.

TABLE XIII

Comparison of Anti-inflammatory Activity of Peptides to CT-112

| Treatment | Thickness Difference (Left - Right) (in) |
|---|---|
| PBS | 0.00658 ± 0.00290 |
| CT-112 | 0.00132 ± 0.00086* |
| CT-125 | 0.00288 ± 0.00075 |
| CT-135 | 0.00178 ± 0.00073* |
| CT-123 | 0.00228 ± 0.00072* |
| CT-127 | 0.00390 ± 0.00112 |
| CT-176 | 0.00220 ± 0.00137 |

Values represent the mean ± SD of 5 animals.
*Indicates significantly different from PBS-treated animals at p ≤ 0.05.

TABLE XIV

Comparison of Anti-inflammatory Activity of Various Peptides to CT-112

| Treatment | Thickness Difference (Left - Right) (in) |
|---|---|
| PBS | 0.00604 ± 0.00067 |
| CT-112 | 0.00134 ± 0.00044** |
| CT-119 | 0.00158 ± 0.00040** |
| CT-120 | 0.00412 ± 0.00168 |
| CT-173 | 0.00252 ± 0.00102** |
| CT-164 | 0.00146 ± 0.00053** |
| CT-220 | 0.00164 ± 0.00160 |

Values represent the mean ± SD of 5 animals.
**Indicates significantly different from PBS-treated animals at p ≤ 0.01.

TABLE XV

Comparison of Anti-inflammatory Activity of Various Peptides to CT-112

| Treatment | Thickness Difference (Left - Right) (in) |
|---|---|
| PBS | 0.00696 ± 0.00212 |
| CT-112 | 0.00154 ± 0.00092** |
| CT-201 | 0.00362 ± 0.00040* |
| CT-183 | 0.00342 ± 0.00077* |
| CT-144 | 0.00344 ± 0.00120* |
| Albumin | 0.00368 ± 0.00105* |

Values represent the mean ± SD of 5 animals.
*Indicates significantly different from PBS-treated animals at p ≤ 0.05.
**Indicates significantly different from PBS-treated animals at p ≤ 0.01.

14.3. Anti-Inflammatory Activity of Blocked, Substituted and Truncated Versions of CT-112

The anti-inflammatory effect of CT-112 (SEQ. ID NO: 1) was compared to that of a variety of CT-112 analogs and derivatives which were either blocked at their amino- or carboxyl-terminal ends, or blocked at both ends, or variously truncated, or in which particular amino acid residues were either substituted or omitted.

14.3.1. Materials and Methods

A first set of CT-112-derivatized peptides was chemically synthesized. These included the CT-112 (SEQ. ID NO: 1) octapeptide with an acetyl group added to the amino-terminal end of the peptide (Ac-Thr-Thr-Ser-Gln-Val-Arg-Pro-Arg) (SEQ ID NO 85), CT-112 (SEQ. ID NO: 1) with an amido group added to the carboxyl-terminal end of the peptide (Thr-Thr-Ser-Gln-Val-Arg-Pro-Arg-$N_2$) (SEQ ID NO 86), and CT-112 (SEQ. ID NO: 1) blocked thus at both ends (Ac-Thr-Thr-Ser-Gln-Val-Arg-Pro-Arg-$NH_2$) (SEQ ID NO 87). In addition, the random octapeptide, CT-120 (Val-Thr-Arg-Pro-Thr-Gln-Arg-Ser) (SEQ. ID NO: 11), used previously as described in Section 14.2, was tested, as was CT-127 (Thr-Thr-Ser-Gly-Ile-His-Pro-Lys) (SEQ. ID NO: 12), which is a peptide derived from connective tissue activating peptide III (CTAPIII), a member of the α-chemokine family.

A second set of CT-112 (SEQ. ID NO: 1) analogous peptides (SEQ. ID NOS: 3, 4, 6, 24–28), all truncated versions of CT-112, was chemically synthesized.

A third set of CT-112 (SEQ ID NO: 1) analogous peptides (SEQ. ID NOS: 25, 26, 29–73) was chemically synthesized. Here, each of the eight amino acid residues comprising CT-112 (SEQ. ID NO: 1) was sequentially either replaced or omitted. In each species of peptide in which a particular residue was replaced, the amino acid residue was replaced either with its D-amino acid counterpart, or with an alanyl, glutamyl, lysyl or leucyl residue.

Peptides in each of the three sets were tested for anti-inflammatory activity using the mouse ear acute inflammation model. The AA challenge was the same as described supra in Example 7. Seven to 10 animals were used for each tested peptide. All animals received a single 6 mg/kg subcutaneous dosing 4 hr prior to challenge with AA. Ear thickness measurements were made 1 hr post-challenge.

14.3.2. Results and Discussion

The results are presented graphically in FIGS. 7–9 and in tabular form in Tables XVI and XVII. For the first set of CT-112-derivatized peptides, blockage of either or both ends of CT-112 (SEQ. ID NO: 1) resulted in significant reduction in the ability of the peptide to inhibit inflammation (FIG. 7, Table XVI). CT-120 (SEQ. ID NO: 11), a random peptide which showed little activity previously, appeared to significantly inhibit inflammation in this study (FIG. 7). In addition, CT-127 (SEQ. ID NO: 12) was significantly effective in inhibiting inflammation. These results indicate that a peptide derived from another α-chemokine was active in inhibiting inflammation.

For the second set of CT-112-analogous peptides (SEQ. ID NOS: 3, 4, 6, 24–28), truncation of either end of the CT-112 (SEQ. ID NO: 1) peptide by one or more amino acid residues significantly reduced the ability of the resulting peptide to inhibit inflammation (FIG. 8, Table XVI). These results indicate that optimal activity of CT-112 (SEQ. ID NO: 1) is best achieved with the intact octapeptide.

For the third set of CT-112 analogous peptides (SEQ. ID NOS: 25, 26, 29–73), the effect of replacement of any of the amino acid residues with its D-amino acid counterpart varied depending upon the residue replaced (FIG. 9, Table XVII). So, e.g., replacement of either L-Thr$_1$ or L-Thr$_2$ with D-Thr results in a peptide which retains substantial anti-inflammatory activity. Replacement of Gln$_4$ or Arg$_8$, however, significantly reduces activity.

Replacing either Thr$_1$ or Ser$_3$ with Ala reduces activity, while replacement of Arg$_6$ with Ala slightly enhanced the anti-inflammatory effect.

Replacing either Thr$_2$ or Arg$_8$ with Glu reduced activity, while replacing Ser$_3$ or Arg$_6$ with Glu slightly enhanced the anti-inflammtory effect.

Replacing amino acid residues with Lys appeared to have little effect generally, although replacement of Thr$_1$ with Lys resulted in decreased activity.

Replacement of either Gln$_4$ or Arg$_8$ with Leu dramatically reduced the activity of the resulting peptide.

Omission of any of the amino acid residues except Pro$_7$ reduced the activity of the resulting peptide.

These results indicate that the activity observed due to CT-112 (SEQ. ID NO: 1) administration is not due to a non-specific effect of a peptide, but rather the activity is related to specific structural features of the molecule. The activity can be either enhanced or reduced by specific changes in the amino acid sequence of the peptide.

TABLE XVI

Effect of Amino Acid Truncation and Terminal Blocking on the Anti-inflammatory Activity of CT-112

| Peptide† | % Inhibition |
|---|---|
| No Treatment | 0.00 |
| Val Arg Pro Arg (4) | 29.7 |
| Gln Val Arg Pro Arg (24) | 37.8 |
| Ser Gln Val Arg Pro Arg (3) | 16.2 |
| Thr Ser Gln Val Arg Pro Arg (25) | 27.0 |
| Thr Thr Ser Gln Val Arg Pro Arg (1) | 64.9 |
| Thr Thr Ser Gln Val Arg Pro (26) | 29.7 |
| Thr Thr Ser Gln Val Arg (27) | 29.7 |
| Thr Thr Ser Gln Val (6) | 10.8 |
| Thr Thr Ser Gln (28) | 29.7 |
| Ac-Thr Thr Ser Gln Val Arg Pro Arg (85) | 29.7 |
| Thr Thr Ser Gln Val Arg Pro Arg-NH$_2$ (86) | 32.4 |
| Ac-Thr Thr Ser Gln Val Arg Pro Arg-NH$_2$ (87) | 13.5 |

†Peptide is designated using the three letter amino acid abbreviations followed by the SEQ. ID. NO. in parentheses.

TABLE XVII

Effect of Amino Acid Substitution on the Anti-inflammatory Activity of CT-112

| Peptide Series with D-Amino Acid Residue Replacement† | % Inhibition |
|---|---|
| (D-Thr) Thr Ser Gln Val Arg Pro Arg (66) | 75.7 |
| Thr (D-Thr) Ser Gln Val Arg Pro Arg (67) | 64.9 |
| Thr Thr (D-Ser) Gln Val Arg Pro Arg (68) | 45.9 |
| Thr Thr Ser (D-Gln) Val Arg Pro Arg (69) | 37.8 |
| Thr Thr Ser Gln (D-Val) Arg Pro Arg (70) | 62.2 |
| Thr Thr Ser Gln Val (D-Arg) Pro Arg (71) | 51.4 |
| Thr Thr Ser Gln Val Arg (D-Pro) Arg (72) | 51.4 |
| Thr Thr Ser Gln Val Arg Pro (D-Arg) (73) | 37.8 |

| Peptide Series with Glutamyl Replacement† | % Inhibition |
|---|---|
| Glu Thr Ser Gln Val Arg Pro Arg (29) | 64.9 |
| Thr Glu Ser Gln Val Arg Pro Arg (30) | 43.2 |
| Thr Thr Glu Gln Val Arg Pro Arg (31) | 81.1 |
| Thr Thr Ser Glu Val Arg Pro Arg (32) | 75.7 |
| Thr Thr Ser Gln Glu Arg Pro Arg (33) | 54.1 |
| Thr Thr Ser Gln Val Glu Pro Arg (34) | 86.5 |
| Thr Thr Ser Gln Val Arg Glu Arg (35) | 62.2 |
| Thr Thr Ser Gln Val Arg Pro Glu (36) | 37.8 |

| Peptide Series with Alanyl Replacement† | % Inhibition |
|---|---|
| Ala Thr Ser Gln Val Arg Pro Arg (37) | 40.5 |
| Thr Ala Ser Gln Val Arg Pro Arg (38) | 62.2 |
| Thr Thr Ala Gln Val Arg Pro Arg (39) | 35.1 |
| Thr Thr Ser Ala Val Arg Pro Arg (40) | 62.2 |
| Thr Thr Ser Gln Ala Arg Pro Arg (41) | 56.8 |
| Thr Thr Ser Gln Val Ala Pro Arg (42) | 75.7 |
| Thr Thr Ser Gln Val Arg Ala Arg (43) | 64.9 |
| Thr Thr Ser Gln Val Arg Pro Ala (44) | 62.2 |

| Peptide Series with Single Amino Acid Residue Omission† | % Inhibition |
|---|---|
| Thr ( ) Ser Gln Val Arg Pro Arg (25) | 27.0 |
| Thr Thr ( ) Gln Val Arg Pro Arg (45) | 24.3 |
| Thr Thr Ser ( ) Val Arg Pro Arg (46) | 37.8 |
| Thr Thr Ser Gln ( ) Arg Pro Arg (47) | 37.8 |
| Thr Thr Ser Gln Val ( ) Pro Arg (48) | 45.9 |
| Thr Thr Ser Gln Val Arg ( ) Arg (49) | 54.1 |
| Thr Thr Ser Gln Val Arg Pro ( ) (26) | 29.7 |

| Peptide Series with Lysyl Replacement† | % Inhibition |
|---|---|
| Lys Thr Ser Gln Val Arg Pro Arg (50) | 32.4 |
| Thr Lys Ser Gln Val Arg Pro Arg (51) | 75.7 |
| Thr Thr Lys Gln Val Arg Pro Arg (52) | 48.6 |
| Thr Thr Ser Lys Val Arg Pro Arg (53) | 70.3 |
| Thr Thr Ser Gln Lys Arg Pro Arg (54) | 73.0 |
| Thr Thr Ser Gln Val Lys Pro Arg (55) | 54.1 |
| Thr Thr Ser Gln Val Arg Lys Arg (56) | 62.2 |
| Thr Thr Ser Gln Val Arg Pro Lys (57) | 70.3 |

| Peptide Series with Leucyl Replacement† | % Inhibition |
|---|---|
| Leu Thr Ser Gln Val Arg Pro Arg (58) | 43.2 |
| Thr Leu Ser Gln Val Arg Pro Arg (59) | 35.1 |
| Thr Thr Leu Gln Val Arg Pro Arg (60) | 43.2 |
| Thr Thr Ser Leu Val Arg Pro Arg (61) | 2.7 |
| Thr Thr Ser Gln Leu Arg Pro Arg (62) | 51.4 |
| Thr Thr Ser Gln Val Leu Pro Arg (63) | 51.4 |
| Thr Thr Ser Gln Val Arg Leu Arg (64) | 54.1 |
| Thr Thr Ser Gln Val Arg Pro Leu (65) | 13.5 |

†Peptide is designated using the three letter amino acid abbreviations followed by the SEQ. ID NO in parentheses.

15. EXAMPLE: EFFECT OF CT-112 ON DELAYED-TYPE HYPERSENSITIVITY

15.1. Materials and Methods

CT-112 (SEQ. ID NO: 1) was tested for its ability to modulate the immune response in a mouse model of delayed hypersensitivity (Filipp et al., 1984, Allergy, 39: 499–507; Diezel et al., 1989 J. Invest. Dermatol. 93:322–326). The mice used in this study were 8-wk old hairless females (Jackson Laboratories). The mice were sensitized to a contact allergen (1-chloro-2,4-dinitrobenzene, DNCB) by painting the dorsothoracic region twice daily for 5 consecutive days with 50 μl of 0.5% DNCB in 75% acetone:25% vegetable oil. The animals were allowed to rest for 24 hr prior to challenge with DNCB. On the sixth day after initiation of the sensitization treatments, the animals were challenged with 50 μl of DNCB solution applied to the left ear. After 24 hrs, the ear thickness was determined and compared to the unchallenged ear.

The treatment groups were as follows:

a) PBS control;

b) Prednisone (intraperitoneal injection of 25 mg/kg, 2 hr prior to challenge);

c) 7-day pump (60 mg CT-112/kg/24 hr);

d) CT-112 (intraperitoneal injections of 60 mg/kg/ injection at 3, 1, and 0.25 hr prior to challenge and 3, 6 and 21 hr post-challenge);

e) DMSO control (topical application of 50 μl at 3, 1 and 0.25 hr prior to challenge; and f) CT-112 in DMSO (20 mg/ml, topical application of 50 μl at 3, 1, and 0.25 hr prior to challenge and 3, 6 and 21 hr post-challenge).

15.2. Results and Discussion

The results are presented in Table XVIII. CT-112 (SEQ. ID NO: 1) was comparable to prednisone in its ability to inhibit delayed-type hypersensitivity induced by DNCB. The group that received topical application of CT-112 (SEQ. ID NO: 1) in DMSO was statistically different from the group that received topical application of vehicle (DMSO) alone. Topical application of CT-112 (SEQ. ID NO: 1) did not result in a statistically significant reduction in delayed-type hypersensitivity when compared to the PBS control group that did not receive topical application of DMSO alone.

The results of this study demonstrate that CT-112 (SEQ. ID NO: 1) is effective in preventing the delayed-type hypersensitivity response when administered systemically. This suggests that the activity of CT-112 (SEQ. ID NO: 1) is not strictly neutrophil-specific, but also affects T-cell mediated immune responses.

TABLE XVIII

Effect of CT-112 on Delayed Type Hypersensitivity

| Treatment Group | Thickness Difference (Left - Right) (in) | % Inhibition of Inflammation |
| --- | --- | --- |
| Control (PBS) pump | 0.00428 ± 0.001578 | 0.0 |
| Prednisone | 0.00014 ± 0.000446** | 96.7 |
| CT-112 pump | 0.00087 ± 0.000398** | 79.7 |
| CT-112 ip | 0.00169 ± 0.000643* | 68.4 |
| DMSO (Control) | 0.00448 ± 0.000693 | -4.7 |
| 2CT-112 top. app in DMSO | 0.00350 ± 0.000408† | 18.2 |

TABLE XVIII-continued

Values represent the mean ± SD of 5 animals.
*Indicates significantly different from control animals at p ≦ 0.05.
**Indicates significantly different from control animals at p ≦ 0.01.
†Indicates significantly different from DMSO-treated animals at p ≦ 0.05.

16. EXAMPLE: EFFECT OF CT-112 ON TYPE-II COLLAGEN IMMUNIZATION INDUCED RHEUMATOID ARTHRITIS

CT-112 (SEQ. ID NO: 1) was tested for effectiveness in inhibiting the development of type-II collagen-induced arthritis (CIA). CIA is an experimental model of arthritis with a number of pathological, immunological and genetic features in common with rheumatoid arthritis (Wooley, 1988 Meth. Enzym. 162: 361–373). CIA is induced by immunization of susceptible strains of mice with type-II collagen. After immunization, a progressive, inflammatory arthritis develops in the majority of immunized animals, which is characterized clinically by erythema and edema. This model was devised to mimic diseases in which an immune response is mounted to the host's own connective tissue molecules, i.e., the type-II collagen found in the articular cartilage (Wooley, 1988, supra).

16.1. Materials and Methods

Mice (DBA/1, 10–12 weeks old, Jackson Laboratories) were randomly assigned to one of 3 groups of 12 animals each. CT-112 (SEQ. ID NO: 1) was prepared for injection by dissolving in sterile PBS. CT-112 (SEQ. ID NO: 1) was administered daily according to the following schedule:

a) Control animals (0.1 ml of sterile PBS) (7 mice);

b) Low dose CT-112 (0.1 ml sterile PBS containing 0.25 mg CT-112 at 10 mg/kg) (8 mice); and c) High dose CT-112 (0.1 ml sterile PBS containing 2.5 mg of CT-112 at 100 mg/kg) (8 mice).

Three days after initial dosing with CT-112 (SEQ. ID NO: 1), all mice were injected intradermally at the base of the tail with 100 μg of bovine type-II collagen in Freund's complete adjuvant. Mice were monitored daily for the onset of disease, and weighed twice weekly with overall health status noted. Arthritis-affected animals were clinically assessed 5 times per week until 10 weeks post-immunization. Paw measurements were taken 3 times per week. Mice lacking signs of arthritis 10 weeks post-immunization were considered disease-free.

All mice were pre-bled prior to the start of the trial, subsequently again at 2 and 4 weeks post-immunization, again at the onset of CIA, and finally at the termination of the study. Sera were separated and stored at −80° C. ELISA assays were performed to determine anti-collagen antibody concentrations. Spleen and lymph nodes were removed at sacrifice, and single cell suspensions prepared therefrom. Mitogen responses to Con A and LPS, as well as antigen-specific responses to type-II collagen, were determined.

Appropriate statistical comparisons (Chi square, Student's T-test and non-parametric median comparisons) were performed using SPSS/PC software to assess the influence of CT-112 (SEQ. ID NO: 1) at both low and high doses on the incidence, onset, severity and progression of collagen-induced arthritis, the antibody response to collagen, T-cell and B-cell mitogen responses, and T-cell specific responses to type-II collagen.

16.2. Results and Discussion

The incidence and onset of CIA is shown in FIG. 10. The onset of arthritis was somewhat retarded by CT-112 (SEQ. ID NO: 1) at both low and high doses compared to control mice. The final incidence of CIA in the control mice (87.5%) was higher than either the high dose mice (50%) or the low dose mice (62.5%). Though neither of these results were significantly different from the control, the incidence of arthritis in the high dose group showed a clear trend towards statistical reduction (p=0.14).

Arthritis in the low dose group progressed to significantly fewer paws (p=0.035) (FIG. 11) and approached statistical significance for reduced disease severity (p=0.058) compared to the control. Analysis of arthritis parameters over time suggested that CT-112 (SEQ. ID NO: 1) at either low or high dose retards the progression of arthritis to uninvolved limbs, and markedly influences the "advance in disease" index that characterizes the evolution from inflammatory disease to erosive joint damage (FIG. 12).

Interestingly, 25% of involved paws in the low dose group were characterized as in remission at the conclusion of the trial, compared to 6.3% of involved paws in the control group. This difference, however, was not statistically significant. Maximum paw swelling was not influenced by CT-112 (SEQ. ID NO: 1).

CT-112 (SEQ. ID NO: 1) at both high and low doses had an effect on the histopathology of CIA (FIG. 13), reducing disease-induced joint erosion and significantly reducing ($p \leq 0.05$) disease-induced loss of joint architecture. The effects of CT-112 (SEQ. ID NO: 1) on synovitis and pannus, however, were not significant. This may be due to the fact that CT-112 (SEQ. ID NO: 1) does not affect all types of inflammatory cells. That is, granulocytes, macrophages, fibroblasts and other cells also associated with inflammation may be unaltered with respect to their response to an inflammatory stimulus. This supports the conclusion that CT-112 (SEQ. ID NO: 1) inhibits specific aspects of the inflammatory response.

CT-112 (SEQ. ID NO: 1) at both high and low doses appears to reduce the anti-collagen antibody titer in mouse serum. Antibody reduction at 4 wks post-immunization was statistically significant in mice from the high dose group (p=0.028) (FIG. 14). The difference in anti-collagen antibody titer was greatest in mice assessed at the onset of disease, although at this time point the difference did not reach statistical significance due to the small sample size.

At the conclusion of the trial, significantly higher antibody titers were observed in mice from the low dose group than in control mice. The decline in control titer, which accounts for this difference, is typical of this model. Therefore the data suggest that CT-112 (SEQ. ID NO: 1) has delayed, rather than inhibited, the serological response to collagen.

Cellular responses to mitogens and antigen (type-II collagen) were similar in lymph node cells from CT-112 (SEQ. ID NO: 1) treated mice and control animals. Spleen cell response to Con A and to LPS in cells from mice treated with CT-112 (SEQ. ID NO: 1) suggested neither immunosuppression nor immunoactivation. The proliferative results were similar between arthritic and non-arthritic mice in all groups.

No changes in hematological profiles were observed, and all animals gained weight at the same rate throughout the study.

17. EXAMPLE: TOXICITY STUDIES

The following example summarizes results obtained in a variety of experiments conducted to assess the toxicity of CT-112 (SEQ. ID NO: 1).

The mutagenic potential of CT-112 (SEQ. ID NO: 1) has been assessed. CT-112 (SEQ. ID NO: 1) at concentrations of 100–5,000 µg/ml, with or without rat liver microsomal enzyme activation, did not cause an increase in the number of revertants (histidine independent growth) in the Salmonella reverse mutation assay (Arnes et al., 1975, Mutation Res. 31:347–364). CT-112 (SEQ. ID NO: 1) at concentrations of 1,260–4,990 µg/ml, with or without rat liver microsomal enzyme activation, did not induce chromosomal aberrations in a Chinese hamster ovary cell assay (Evans, H. J., 1962, Int. Rev. Cyt. 13:221–321).

CT-112 (SEQ. ID NO: 1) at concentrations of 500–5,000 µg/ml, with or without rat liver microsomal enzyme activation, did not cause forward mutations in Chinese hamster ovary cells that are hypoxanthine-guanine phosphoribosyl transferase positive (HGPRT). Forward mutations of these cells would cause the loss of the ability to express HGPRT and the cells would become insensitive to toxic purine analogs (Hsie et al., 1975, Somat. Cell Genet. 1:247–261).

CT-112 (SEQ. ID NO: 1) at concentrations of 62.5, 125 and 250 mg/kg did not induce a significant increase in micronuclei after 24, 48 or 72 hr in a mouse bone marrow polychromatic erythrocyte assay (Heddle et al., 1983, Mut. Res. 123: 61–118).

Acute toxicity of CT-112 (SEQ. ID NO: 1) in mice and rats was assessed. Mice were dosed by intravenous injection with CT-112 (SEQ. ID NO: 1) at 100, 500 or 1,000 mg/kg. Minimal transient clinical effects (hypoactivity and hypersensitivity) were noted on the day of treatment in one mouse treated at 500 mg/kg and in two mice treated at 1,000 mg/kg, which mice returned to normal appearance the day after treatment. There were no statistical differences in mean body weight or in mean body weight gain between control and treated groups. No lesions were visible at necropsy for any of the mice.

Rats were dosed with CT-112 (SEQ. ID NO: 1) at 100, 500 or 1,000 mg/kg. Transient clinical effects (hypoactivity, hypersensitiviy, staggered gait, cyanosis and absence of righting reflex) were noted on the day of treatment in several rats treated at 500 mg/kg and 1,000 mg/kg. All rats returned to normal appearance the day after treatment. There were no statistical differences in mean body weight or in mean body weight gain between control and treated groups. No lesions were visible at necropsy for any of the rats.

The present invention has been described in detail with particular reference to the above embodiments. It will be understood, however, that the present invention is not to be limited in scope by the embodiments disclosed which are intended as illustrations of aspects of the invention.

Indeed, various modifications of the invention in addition to those shown and described herein will become apparent to those skilled in the art from the foregoing description. Such modifications are intended to fall within the scope of the appended claims.

Various references have been cited herein; these are incorporated by reference, in their entirety.

SEQUENCE LISTING ( 1 ) GENERAL INFORMATION:

( i i i ) NUMBER OF SEQUENCES: 91

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Thr Thr Ser Gln Val Arg Pro Arg
1               5

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:2:

Val Lys Thr Thr Ser Gln Val Arg Pro Arg
1               5                   10

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:3:

Ser Gln Val Arg Pro Arg
1               5

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:4:

Val Arg Pro Arg
1

( 2 ) INFORMATION FOR SEQ ID NO:5:

( i ) SEQUENCE CHARACTERISTICS:
        ( A ) LENGTH: 11 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:5:

Thr Thr Ser Gln Val Arg Pro Arg His Ile Thr
1               5                       10

( 2 ) INFORMATION FOR SEQ ID NO:6:

( i ) SEQUENCE CHARACTERISTICS:
        ( A ) LENGTH: 5 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:6:

Thr Thr Ser Gln Val
1               5

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:7:

Thr Ser Gln Val Arg
1               5

( 2 ) INFORMATION FOR SEQ ID NO:8:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:8:

Thr Thr Ser Gly Ile His Pro Lys
1               5

(2) INFORMATION FOR SEQ ID NO:9:

(i) SEQUENCE CHARACTERISTICS:
        (A) LENGTH: 70 amino acids
        (B) TYPE: amino acid
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:9:

```
Glu Ala Glu Glu Asp Gly Asp Leu Gln Cys Leu Cys Val Lys Thr Thr
 1               5                  10                  15

Ser Gln Val Arg Pro Arg His Ile Thr Ser Leu Glu Val Ile Lys Ala
             20                  25                  30

Gly Pro His Cys Pro Thr Ala Gln Leu Ile Ala Thr Leu Lys Asn Gly
         35                  40                  45

Arg Lys Ile Cys Leu Asp Leu Gln Ala Pro Leu Tyr Lys Lys Ile Ile
     50                  55                  60

Lys Lys Leu Leu Glu Ser
 65              70
```

(2) INFORMATION FOR SEQ ID NO:10:

(i) SEQUENCE CHARACTERISTICS:
        (A) LENGTH: 4 amino acids
        (B) TYPE: amino acid
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:10:

```
Thr Thr Ser Gln
 1
```

(2) INFORMATION FOR SEQ ID NO:11:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:11:

```
Val Thr Arg Pro Thr Gln Arg Ser
 1               5
```

(2) INFORMATION FOR SEQ ID NO:12:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (iii) HYPOTHETICAL: NO (i v) ANTI-SENSE: NO (x i) SEQUENCE DESCRIPTION: SEQ ID NO:12:

Thr Thr Ser Gly Ile His Pro Lys
1               5

(2) INFORMATION FOR SEQ ID NO:13:

(i) SEQUENCE CHARACTERISTICS:
      (A) LENGTH: 8 amino acids
      (B) TYPE: amino acid
      (D) TOPOLOGY: unknown (i i) MOLECULE TYPE: peptide (i i i) HYPOTHETICAL: NO (i v) ANTI-SENSE: NO (x i) SEQUENCE DESCRIPTION: SEQ ID NO:13:

Thr Tyr Ser Lys Pro Phe His Lys
1               5

(2) INFORMATION FOR SEQ ID NO:14:

(i) SEQUENCE CHARACTERISTICS:
      (A) LENGTH: 8 amino acids
      (B) TYPE: amino acid
      (D) TOPOLOGY: unknown (i i) MOLECULE TYPE: peptide (i i i) HYPOTHETICAL: NO (i v) ANTI-SENSE: NO (x i) SEQUENCE DESCRIPTION: SEQ ID NO:14:

Thr Leu Gln Gly Ile His Pro Lys
1               5

(2) INFORMATION FOR SEQ ID NO:15:

(i) SEQUENCE CHARACTERISTICS:
      (A) LENGTH: 9 amino acids
      (B) TYPE: amino acid
      (D) TOPOLOGY: unknown (i i) MOLECULE TYPE: peptide (i i i) HYPOTHETICAL: NO (i v) ANTI-SENSE: NO (x i) SEQUENCE DESCRIPTION: SEQ ID NO:15:

Gln Val Lys Thr Val Lys Gln Val Ser
1               5

(2) INFORMATION FOR SEQ ID NO:16:

(i) SEQUENCE CHARACTERISTICS:
      (A) LENGTH: 8 amino acids
      (B) TYPE: amino acid
      (D) TOPOLOGY: unknown (i i) MOLECULE TYPE: peptide (i i i) HYPOTHETICAL: NO (i v) ANTI-SENSE: NO (x i) SEQUENCE DESCRIPTION: SEQ ID NO:16:

```
Thr Thr Gln Gly Val His Pro Lys
 1               5
```

( 2 ) INFORMATION FOR SEQ ID NO:17:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:17:

```
Tyr Ile Ala Arg Pro Leu Pro Arg
 1               5
```

( 2 ) INFORMATION FOR SEQ ID NO:18:

( i ) SEQUENCE CHARACTERISTICS:
        ( A ) LENGTH: 10 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:18:

```
Tyr Thr Ala Arg Lys Leu Pro Arg Asn Phe
 1               5                   1 0
```

( 2 ) INFORMATION FOR SEQ ID NO:19:

( i ) SEQUENCE CHARACTERISTICS:
        ( A ) LENGTH: 9 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:19:

```
Tyr Thr Arg Glu Ala Ser Ser Asn Phe
 1               5
```

( 2 ) INFORMATION FOR SEQ ID NO:20:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:20:

```
Thr Thr Ser His Val Lys Pro Gln
 1               5
```

( 2 ) INFORMATION FOR SEQ ID NO:21:

( i ) SEQUENCE CHARACTERISTICS:
        ( A ) LENGTH: 9 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:21:

Thr His Val Leu Leu Thr His Thr Ile
    1                5

( 2 ) INFORMATION FOR SEQ ID NO:22:

( i ) SEQUENCE CHARACTERISTICS:
        ( A ) LENGTH: 14 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:22:

Val Gln Val Arg Lys Ile Glu Ile Val Arg Lys Lys Pro Ile
    1                5                            10

( 2 ) INFORMATION FOR SEQ ID NO:23:

( i ) SEQUENCE CHARACTERISTICS:
        ( A ) LENGTH: 9 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:23:

Thr Thr Ser Leu Asn Pro Asp Tyr Arg
    1                5

( 2 ) INFORMATION FOR SEQ ID NO:24:

( i ) SEQUENCE CHARACTERISTICS:
        ( A ) LENGTH: 5 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:24:

Gln Val Arg Pro Arg
    1                5

( 2 ) INFORMATION FOR SEQ ID NO:25:

( i ) SEQUENCE CHARACTERISTICS:
        ( A ) LENGTH: 7 amino acids ( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:25:

Thr Ser Gln Val Arg Pro Arg
1               5

( 2 ) INFORMATION FOR SEQ ID NO:26:

( i ) SEQUENCE CHARACTERISTICS:
      ( A ) LENGTH: 7 amino acids
      ( B ) TYPE: amino acid
      ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:26:

Thr Thr Ser Gln Val Arg Pro
1               5

( 2 ) INFORMATION FOR SEQ ID NO:27:

( i ) SEQUENCE CHARACTERISTICS:
      ( A ) LENGTH: 6 amino acids
      ( B ) TYPE: amino acid
      ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:27:

Thr Thr Ser Gln Val Arg
1               5

( 2 ) INFORMATION FOR SEQ ID NO:28:

( i ) SEQUENCE CHARACTERISTICS:
      ( A ) LENGTH: 4 amino acids
      ( B ) TYPE: amino acid
      ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:28:

Thr Thr Ser Gln
1

( 2 ) INFORMATION FOR SEQ ID NO:29:

( i ) SEQUENCE CHARACTERISTICS:
      ( A ) LENGTH: 8 amino acids
      ( B ) TYPE: amino acid
      ( D ) TOPOLOGY: unknown ( i i ) MOLECULE TYPE: peptide (i i i) HYPOTHETICAL: NO (i v) ANTI-SENSE: NO (x i) SEQUENCE DESCRIPTION: SEQ ID NO:29:

Glu Thr Ser Gln Val Arg Pro Arg
1               5

(2) INFORMATION FOR SEQ ID NO:30:

(i) SEQUENCE CHARACTERISTICS:
      (A) LENGTH: 8 amino acids
      (B) TYPE: amino acid
      (D) TOPOLOGY: unknown (i i) MOLECULE TYPE: peptide (i i i) HYPOTHETICAL: NO (i v) ANTI-SENSE: NO (x i) SEQUENCE DESCRIPTION: SEQ ID NO:30:

Thr Glu Ser Gln Val Arg Pro Arg
1               5

(2) INFORMATION FOR SEQ ID NO:31:

(i) SEQUENCE CHARACTERISTICS:
      (A) LENGTH: 8 amino acids
      (B) TYPE: amino acid
      (D) TOPOLOGY: unknown (i i) MOLECULE TYPE: peptide (i i i) HYPOTHETICAL: NO (i v) ANTI-SENSE: NO (x i) SEQUENCE DESCRIPTION: SEQ ID NO:31:

Thr Thr Glu Gln Val Arg Pro Arg
1               5

(2) INFORMATION FOR SEQ ID NO:32:

(i) SEQUENCE CHARACTERISTICS:
      (A) LENGTH: 8 amino acids
      (B) TYPE: amino acid
      (D) TOPOLOGY: unknown (i i) MOLECULE TYPE: peptide (i i i) HYPOTHETICAL: NO (i v) ANTI-SENSE: NO (x i) SEQUENCE DESCRIPTION: SEQ ID NO:32:

Thr Thr Ser Glu Val Arg Pro Arg
1               5

(2) INFORMATION FOR SEQ ID NO:33:

(i) SEQUENCE CHARACTERISTICS:
      (A) LENGTH: 8 amino acids
      (B) TYPE: amino acid
      (D) TOPOLOGY: unknown (i i) MOLECULE TYPE: peptide (i i i) HYPOTHETICAL: NO (i v) ANTI-SENSE: NO ( x i ) SEQUENCE DESCRIPTION: SEQ ID NO:33:

Thr Thr Ser Gln Glu Arg Pro Arg
1               5

( 2 ) INFORMATION FOR SEQ ID NO:34:

( i ) SEQUENCE CHARACTERISTICS:
      ( A ) LENGTH: 8 amino acids
      ( B ) TYPE: amino acid
      ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:34:

Thr Thr Ser Gln Val Glu Pro Arg
1               5

( 2 ) INFORMATION FOR SEQ ID NO:35:

( i ) SEQUENCE CHARACTERISTICS:
      ( A ) LENGTH: 8 amino acids
      ( B ) TYPE: amino acid
      ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:35:

Thr Thr Ser Gln Val Arg Glu Arg
1               5

( 2 ) INFORMATION FOR SEQ ID NO:36:

( i ) SEQUENCE CHARACTERISTICS:
      ( A ) LENGTH: 8 amino acids
      ( B ) TYPE: amino acid
      ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:36:

Thr Thr Ser Gln Val Arg Pro Glu
1               5

( 2 ) INFORMATION FOR SEQ ID NO:37:

( i ) SEQUENCE CHARACTERISTICS:
      ( A ) LENGTH: 8 amino acids
      ( B ) TYPE: amino acid
      ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:37:

Ala Thr Ser Gln Val Arg Pro Arg (2) INFORMATION FOR SEQ ID NO:38:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:38:

Thr Ala Ser Gln Val Arg Pro Arg
    1               5

(2) INFORMATION FOR SEQ ID NO:39:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:39:

Thr Thr Ala Gln Val Arg Pro Arg
    1               5

(2) INFORMATION FOR SEQ ID NO:40:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:40:

Thr Thr Ser Ala Val Arg Pro Arg
    1               5

(2) INFORMATION FOR SEQ ID NO:41:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:41:

Thr Thr Ser Gln Ala Arg Pro Arg
    1               5

(2) INFORMATION FOR SEQ ID NO:42:

( i ) SEQUENCE CHARACTERISTICS:
( A ) LENGTH: 8 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:42:

Thr Thr Ser Gln Val Ala Pro Arg
1               5

( 2 ) INFORMATION FOR SEQ ID NO:43:

( i ) SEQUENCE CHARACTERISTICS:
( A ) LENGTH: 8 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:43:

Thr Thr Ser Gln Val Arg Ala Arg
1               5

( 2 ) INFORMATION FOR SEQ ID NO:44:

( i ) SEQUENCE CHARACTERISTICS:
( A ) LENGTH: 8 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:44:

Thr Thr Ser Gln Val Arg Pro Ala
1               5

( 2 ) INFORMATION FOR SEQ ID NO:45:

( i ) SEQUENCE CHARACTERISTICS:
( A ) LENGTH: 7 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:45:

Thr Thr Gln Val Arg Pro Arg
1               5

( 2 ) INFORMATION FOR SEQ ID NO:46:

( i ) SEQUENCE CHARACTERISTICS:
( A ) LENGTH: 7 amino acids
( B ) TYPE: amino acid ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:46:

Thr  Thr  Ser  Val  Arg  Pro  Arg
        1                   5

( 2 ) INFORMATION FOR SEQ ID NO:47:

( i ) SEQUENCE CHARACTERISTICS:
             ( A ) LENGTH: 7 amino acids
             ( B ) TYPE: amino acid
             ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:47:

Thr  Thr  Ser  Gln  Arg  Pro  Arg
        1                   5

( 2 ) INFORMATION FOR SEQ ID NO:48:

( i ) SEQUENCE CHARACTERISTICS:
             ( A ) LENGTH: 7 amino acids
             ( B ) TYPE: amino acid
             ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:48:

Thr  Thr  Ser  Gln  Val  Pro  Arg
        1                   5

( 2 ) INFORMATION FOR SEQ ID NO:49:

( i ) SEQUENCE CHARACTERISTICS:
             ( A ) LENGTH: 7 amino acids
             ( B ) TYPE: amino acid
             ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:49:

Thr  Thr  Ser  Gln  Val  Arg  Arg
        1                   5

( 2 ) INFORMATION FOR SEQ ID NO:50:

( i ) SEQUENCE CHARACTERISTICS:
             ( A ) LENGTH: 8 amino acids
             ( B ) TYPE: amino acid
             ( D ) TOPOLOGY: unknown ( i i ) MOLECULE TYPE: peptide (iii) HYPOTHETICAL: NO (iv) ANTI-SENSE: NO (xi) SEQUENCE DESCRIPTION: SEQ ID NO:50:

Lys Thr Ser Gln Val Arg Pro Arg
1               5

(2) INFORMATION FOR SEQ ID NO:51:

(i) SEQUENCE CHARACTERISTICS:
  (A) LENGTH: 8 amino acids
  (B) TYPE: amino acid
  (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:51:

Thr Lys Ser Gln Val Arg Pro Arg
1               5

(2) INFORMATION FOR SEQ ID NO:52:

(i) SEQUENCE CHARACTERISTICS:
  (A) LENGTH: 8 amino acids
  (B) TYPE: amino acid
  (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:52:

Thr Thr Lys Gln Val Arg Pro Arg
1               5

(2) INFORMATION FOR SEQ ID NO:53:

(i) SEQUENCE CHARACTERISTICS:
  (A) LENGTH: 8 amino acids
  (B) TYPE: amino acid
  (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:53:

Thr Thr Ser Lys Val Arg Pro Arg
1               5

(2) INFORMATION FOR SEQ ID NO:54:

(i) SEQUENCE CHARACTERISTICS:
  (A) LENGTH: 8 amino acids
  (B) TYPE: amino acid
  (D) TOPOLOGY: unknown (ii) MOLECULE TYPE: peptide (iii) HYPOTHETICAL: NO (iv) ANTI-SENSE: NO ( x i ) SEQUENCE DESCRIPTION: SEQ ID NO:54:

Thr Thr Ser Gln Lys Arg Pro Arg
1               5

( 2 ) INFORMATION FOR SEQ ID NO:55:

( i ) SEQUENCE CHARACTERISTICS:
      ( A ) LENGTH: 8 amino acids
      ( B ) TYPE: amino acid
      ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:55:

Thr Thr Ser Gln Val Lys Pro Arg
1               5

( 2 ) INFORMATION FOR SEQ ID NO:56:

( i ) SEQUENCE CHARACTERISTICS:
      ( A ) LENGTH: 8 amino acids
      ( B ) TYPE: amino acid
      ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:56:

Thr Thr Ser Gln Val Arg Lys Arg
1               5

( 2 ) INFORMATION FOR SEQ ID NO:57:

( i ) SEQUENCE CHARACTERISTICS:
      ( A ) LENGTH: 8 amino acids
      ( B ) TYPE: amino acid
      ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:57:

Thr Thr Ser Gln Val Arg Pro Lys
1               5

( 2 ) INFORMATION FOR SEQ ID NO:58:

( i ) SEQUENCE CHARACTERISTICS:
      ( A ) LENGTH: 8 amino acids
      ( B ) TYPE: amino acid
      ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:58:

Leu Thr Ser Gln Val Arg Pro Arg
1               5

(2) INFORMATION FOR SEQ ID NO:59:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:59:

```
Thr Leu Ser Gln Val Arg Pro Arg
1               5
```

(2) INFORMATION FOR SEQ ID NO:60:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:60:

```
Thr Thr Leu Gln Val Arg Pro Arg
1               5
```

(2) INFORMATION FOR SEQ ID NO:61:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:61:

```
Thr Thr Ser Leu Val Arg Pro Arg
1               5
```

(2) INFORMATION FOR SEQ ID NO:62:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:62:

```
Thr Thr Ser Gln Leu Arg Pro Arg
1               5
```

(2) INFORMATION FOR SEQ ID NO:63:

( i ) SEQUENCE CHARACTERISTICS:
: ( A ) LENGTH: 8 amino acids
: ( B ) TYPE: amino acid
: ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:63:

```
Thr Thr Ser Gln Val Leu Pro Arg
1               5
```

( 2 ) INFORMATION FOR SEQ ID NO:64:

: ( i ) SEQUENCE CHARACTERISTICS:
:: ( A ) LENGTH: 8 amino acids
:: ( B ) TYPE: amino acid
:: ( D ) TOPOLOGY: unknown : ( i i ) MOLECULE TYPE: peptide : ( i i i ) HYPOTHETICAL: NO : ( i v ) ANTI-SENSE: NO : ( x i ) SEQUENCE DESCRIPTION: SEQ ID NO:64:

```
Thr Thr Ser Gln Val Arg Leu Arg
1               5
```

( 2 ) INFORMATION FOR SEQ ID NO:65:

: ( i ) SEQUENCE CHARACTERISTICS:
:: ( A ) LENGTH: 8 amino acids
:: ( B ) TYPE: amino acid
:: ( D ) TOPOLOGY: unknown : ( i i ) MOLECULE TYPE: peptide : ( i i i ) HYPOTHETICAL: NO : ( i v ) ANTI-SENSE: NO : ( x i ) SEQUENCE DESCRIPTION: SEQ ID NO:65:

```
Thr Thr Ser Gln Val Arg Pro Leu
1               5
```

( 2 ) INFORMATION FOR SEQ ID NO:66:

: ( i ) SEQUENCE CHARACTERISTICS:
:: ( A ) LENGTH: 8 amino acids
:: ( B ) TYPE: amino acid
:: ( D ) TOPOLOGY: unknown : ( i i ) MOLECULE TYPE: peptide : ( i i i ) HYPOTHETICAL: NO : ( i v ) ANTI-SENSE: NO : ( i x ) FEATURE:
:: ( A ) NAME/KEY: Modified-site
:: ( B ) LOCATION: 1
:: ( D ) OTHER INFORMATION: /label= D- Thr
::: / note= "Xaa = D-Threonine"

: ( x i ) SEQUENCE DESCRIPTION: SEQ ID NO:66:

```
Xaa Thr Ser Gln Val Arg Pro Arg
1               5
```

( 2 ) INFORMATION FOR SEQ ID NO:67:

( i ) SEQUENCE CHARACTERISTICS:
　　　　　　　　( A ) LENGTH: 8 amino acids
　　　　　　　　( B ) TYPE: amino acid
　　　　　　　　( D ) TOPOLOGY: unknown ( i i ) MOLECULE TYPE: peptide ( i i i ) HYPOTHETICAL: NO ( i v ) ANTI-SENSE: NO ( i x ) FEATURE:
　　　　　　　　( A ) NAME/KEY: Modified-site
　　　　　　　　( B ) LOCATION: 2
　　　　　　　　( D ) OTHER INFORMATION: /label= D- Thr
　　　　　　　　　　　　/ note= "Xaa = D-Threonine"

( x i ) SEQUENCE DESCRIPTION: SEQ ID NO:67:

Thr Xaa Ser Gln Val Arg Pro Arg
1               5

( 2 ) INFORMATION FOR SEQ ID NO:68:

( i ) SEQUENCE CHARACTERISTICS:
　　　　　　　　( A ) LENGTH: 8 amino acids
　　　　　　　　( B ) TYPE: amino acid
　　　　　　　　( D ) TOPOLOGY: unknown ( i i ) MOLECULE TYPE: peptide ( i i i ) HYPOTHETICAL: NO ( i v ) ANTI-SENSE: NO ( i x ) FEATURE:
　　　　　　　　( A ) NAME/KEY: Modified-site
　　　　　　　　( B ) LOCATION: 3
　　　　　　　　( D ) OTHER INFORMATION: /label= D- Ser
　　　　　　　　　　　　/ note= "Xaa = D-Serine"

( x i ) SEQUENCE DESCRIPTION: SEQ ID NO:68:

Thr Thr Xaa Gln Val Arg Pro Arg
1               5

( 2 ) INFORMATION FOR SEQ ID NO:69:

( i ) SEQUENCE CHARACTERISTICS:
　　　　　　　　( A ) LENGTH: 8 amino acids
　　　　　　　　( B ) TYPE: amino acid
　　　　　　　　( D ) TOPOLOGY: unknown ( i i ) MOLECULE TYPE: peptide ( i i i ) HYPOTHETICAL: NO ( i v ) ANTI-SENSE: NO ( i x ) FEATURE:
　　　　　　　　( A ) NAME/KEY: Modified-site
　　　　　　　　( B ) LOCATION: 4
　　　　　　　　( D ) OTHER INFORMATION: /label= D- Gln
　　　　　　　　　　　　/ note= "Xaa = D-Glutamine"

( x i ) SEQUENCE DESCRIPTION: SEQ ID NO:69:

Thr Thr Ser Xaa Val Arg Pro Arg
1               5

( 2 ) INFORMATION FOR SEQ ID NO:70:

( i ) SEQUENCE CHARACTERISTICS:
　　　　　　　　( A ) LENGTH: 8 amino acids
　　　　　　　　( B ) TYPE: amino acid (D) TOPOLOGY: unknown (i i) MOLECULE TYPE: peptide (i i i) HYPOTHETICAL: NO (i v) ANTI-SENSE: NO (i x) FEATURE:
    (A) NAME/KEY: Modified-site
    (B) LOCATION: 5
    (D) OTHER INFORMATION: /label= D- Val
        / note= "Xaa = D-Valine"

(x i) SEQUENCE DESCRIPTION: SEQ ID NO:70:

Thr Thr Ser Gln Xaa Arg Pro Arg
1               5

(2) INFORMATION FOR SEQ ID NO:71:

(i) SEQUENCE CHARACTERISTICS:
        (A) LENGTH: 8 amino acids
        (B) TYPE: amino acid
        (D) TOPOLOGY: unknown (i i) MOLECULE TYPE: peptide (i i i) HYPOTHETICAL: NO (i v) ANTI-SENSE: NO (i x) FEATURE:
        (A) NAME/KEY: Modified-site
        (B) LOCATION: 6
        (D) OTHER INFORMATION: /label= D- Arg
            / note= "Xaa = D-Arginine"

(x i) SEQUENCE DESCRIPTION: SEQ ID NO:71:

Thr Thr Ser Gln Val Xaa Pro Arg
1               5

(2) INFORMATION FOR SEQ ID NO:72:

(i) SEQUENCE CHARACTERISTICS:
        (A) LENGTH: 8 amino acids
        (B) TYPE: amino acid
        (D) TOPOLOGY: unknown (i i) MOLECULE TYPE: peptide (i i i) HYPOTHETICAL: NO (i v) ANTI-SENSE: NO (i x) FEATURE:
        (A) NAME/KEY: Modified-site
        (B) LOCATION: 7
        (D) OTHER INFORMATION: /label= D- Pro
            / note= "Xaa = D-Proline"

(x i) SEQUENCE DESCRIPTION: SEQ ID NO:72:

Thr Thr Ser Gln Val Arg Xaa Arg
1               5

(2) INFORMATION FOR SEQ ID NO:73:

(i) SEQUENCE CHARACTERISTICS:
        (A) LENGTH: 8 amino acids
        (B) TYPE: amino acid
        (D) TOPOLOGY: unknown (i i) MOLECULE TYPE: peptide (i i i) HYPOTHETICAL: NO ( i v ) ANTI-SENSE: NO ( i x ) FEATURE:
       ( A ) NAME/KEY: Modified-site
       ( B ) LOCATION: 8
       ( D ) OTHER INFORMATION: /label= D- Arg
              / note= "Xaa = D-Arginine"

( x i ) SEQUENCE DESCRIPTION: SEQ ID NO:73:

Thr Thr Ser Gln Val Arg Pro Xaa
1               5

( 2 ) INFORMATION FOR SEQ ID NO:74:

( i ) SEQUENCE CHARACTERISTICS:
       ( A ) LENGTH: 8 amino acids
       ( B ) TYPE: amino acid
       ( D ) TOPOLOGY: unknown ( i i ) MOLECULE TYPE: peptide ( i x ) FEATURE:
       ( A ) NAME/KEY: Modified-site
       ( B ) LOCATION: 1
       ( D ) OTHER INFORMATION: /note= "Xaa is nothing or L-Thr"

( i x ) FEATURE:
       ( A ) NAME/KEY: Modified-site
       ( B ) LOCATION: 1
       ( D ) OTHER INFORMATION: /note= "N-terminally attached to
              the Thr is either H or R'-(C=O)-, where R'is selected
              from the group consisting of a lower alkyl, a cycloalkyl,
              an aryl and a heteroaryl, wherein the aryl or heteroaryl
              is either unsubstituted or substituted with a halogen,
              methoxy, amino or alkyl functional group"

( i x ) FEATURE:
       ( A ) NAME/KEY: Modified-site
       ( B ) LOCATION: 2
       ( D ) OTHER INFORMATION: /note= "Xaa is selected from the
              group consisting of nothing, Thr, Lys, Orn, Met, Arg,
              Ser, Trp, Tyr, Cys or His"

( i x ) FEATURE:
       ( A ) NAME/KEY: Modified-site
       ( B ) LOCATION: 3
       ( D ) OTHER INFORMATION: /note= "Xaa is selected from the
              group consisting of nothing, Ser, Glu, Asp, Asn, Gln,
              Cys, His, Lys, Orn, Thr, Trp, or Tyr."

( i x ) FEATURE:
       ( A ) NAME/KEY: Modified-site
       ( B ) LOCATION: 4
       ( D ) OTHER INFORMATION: /note= "Xaa is selected from the
              group consisting of nothing, Gln, Lys, Orn, Arg, Asp,
              Cys, Glu, His, Met, Ser, Thr or Tyr."

( i x ) FEATURE:
       ( A ) NAME/KEY: Modified-site
       ( B ) LOCATION: 5
       ( D ) OTHER INFORMATION: /note= "Xaa is either nothing or
              any naturally occuring amino acid"

( i x ) FEATURE:
       ( A ) NAME/KEY: Modified-site
       ( B ) LOCATION: 6
       ( D ) OTHER INFORMATION: /note= "Xaa is either nothing or
              any naturally occuring amino acid"

( i x ) FEATURE:
       ( A ) NAME/KEY: Modified-site
       ( B ) LOCATION: 7
       ( D ) OTHER INFORMATION: /note= "Xaa is either nothing or
              any naturally occuring amino acid"

( i x ) FEATURE:
       ( A ) NAME/KEY: Modified-site

-continued ( B ) LOCATION: 8
                    ( D ) OTHER INFORMATION: /note= "Xaa is selected from the
                        group consisting of nothing, Arg, Lys, Orn, Asn, Asp,
                        Cys, Glu, His, Met, Ser or Tyr."

( i x ) FEATURE:
                    ( A ) NAME/KEY: Modified-site
                    ( B ) LOCATION: 8
                    ( D ) OTHER INFORMATION: /note= "C-terminally bound to this
                        amino acid is R", which is selected from the group
                        consisting of OH, an amide, a lower alkyl ester, a
                        cycloalkyl ester, an aryl ester, and a heteroaryl ester,
                        wherein the aryl or heteroaryl ester is either
                        unsubstituted or substituted with a halogen, methoxy,
                        amino or alkyl functional group"

( x i ) SEQUENCE DESCRIPTION: SEQ ID NO:74:

Xaa Xaa Xaa Xaa Xaa Xaa Xaa Xaa
        1                   5

( 2 ) INFORMATION FOR SEQ ID NO:75:

( i ) SEQUENCE CHARACTERISTICS:
                    ( A ) LENGTH: 8 amino acids
                    ( B ) TYPE: amino acid
                    ( D ) TOPOLOGY: unknown ( i i ) MOLECULE TYPE: peptide ( i x ) FEATURE:
                    ( A ) NAME/KEY: Modified-site
                    ( B ) LOCATION: 2
                    ( D ) OTHER INFORMATION: /note= "Xaa is selected from Lys,
                        Orn, Met, Arg, Ser, Trp, Tyr, Cys, and His."

( x i ) SEQUENCE DESCRIPTION: SEQ ID NO:75:

Thr Xaa Ser Gln Val Arg Pro Arg
        1                   5

( 2 ) INFORMATION FOR SEQ ID NO:76:

( i ) SEQUENCE CHARACTERISTICS:
                    ( A ) LENGTH: 8 amino acids
                    ( B ) TYPE: amino acid
                    ( D ) TOPOLOGY: unknown ( i i ) MOLECULE TYPE: peptide ( i x ) FEATURE:
                    ( A ) NAME/KEY: Modified-site
                    ( B ) LOCATION: 3
                    ( D ) OTHER INFORMATION: /note= "Xaa is selected from Glu,
                        Asp, Asn, Gln, Cys, His, Orn, Thr, Trp, and Tyr."

( x i ) SEQUENCE DESCRIPTION: SEQ ID NO:76:

Thr Thr Xaa Gln Val Arg Pro Arg
        1                   5

( 2 ) INFORMATION FOR SEQ ID NO:77:

( i ) SEQUENCE CHARACTERISTICS:
                    ( A ) LENGTH: 8 amino acids
                    ( B ) TYPE: amino acid
                    ( D ) TOPOLOGY: unknown ( i i ) MOLECULE TYPE: peptide ( i x ) FEATURE:
                    ( A ) NAME/KEY: Modified-site
                    ( B ) LOCATION: 4
                    ( D ) OTHER INFORMATION: /note= "Xaa is selected from Lys,
                        Orn, Arg, Asp, Cys, Glu, His, Met, Ser, Thr and Tyr."

( x i ) SEQUENCE DESCRIPTION: SEQ ID NO:77:

```
Thr Thr Ser Xaa Val Arg Pro Arg
1               5
```

( 2 ) INFORMATION FOR SEQ ID NO:78:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 5
        ( D ) OTHER INFORMATION: /note= "Xaa can be any amino acid except Val or no amino acid"

( x i ) SEQUENCE DESCRIPTION: SEQ ID NO:78:

```
Thr Thr Ser Gln Xaa Arg Pro Arg
1               5
```

( 2 ) INFORMATION FOR SEQ ID NO:79:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 6
        ( D ) OTHER INFORMATION: /note= "Xaa can be any amino acid except Arg or no amino acid."

( x i ) SEQUENCE DESCRIPTION: SEQ ID NO:79:

```
Thr Thr Ser Gln Val Xaa Pro Arg
1               5
```

( 2 ) INFORMATION FOR SEQ ID NO:80:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 7
        ( D ) OTHER INFORMATION: /note= "Xaa can be any amino acid except Pro or no amino acid."

( x i ) SEQUENCE DESCRIPTION: SEQ ID NO:80:

```
Thr Thr Ser Gln Val Arg Xaa Arg
1               5
```

( 2 ) INFORMATION FOR SEQ ID NO:81:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 8

( D ) OTHER INFORMATION: /note= "Xaa is selected from
either Lys, Orn, Asn, Asp, Cys, Glu, His, Met, Ser, and
Tyr or no amino acid."

( x i ) SEQUENCE DESCRIPTION: SEQ ID NO:81:

Thr Thr Ser Gln Val Arg Pro Xaa
1               5

( 2 ) INFORMATION FOR SEQ ID NO:82:

( i ) SEQUENCE CHARACTERISTICS:
    ( A ) LENGTH: 8 amino acids
    ( B ) TYPE: amino acid
    ( D ) TOPOLOGY: unknown ( i i ) MOLECULE TYPE: peptide ( i x ) FEATURE:
    ( A ) NAME/KEY: Modified-site
    ( B ) LOCATION: 1
    ( D ) OTHER INFORMATION: /note= "R-(C=O)- is terminally
        linked to the amino group of Thr, where R is selected
        from the group consisting of a lower alkyl, a cycloalkyl,
        an aryl and a heteroaryl, wherein the aryl or heteroaryl
        is either unsubstituted or substituted with a halogen,
        methoxy, amino or alkyl functional group."

( x i ) SEQUENCE DESCRIPTION: SEQ ID NO:82:

Thr Thr Ser Gln Val Arg Pro Arg
1               5

( 2 ) INFORMATION FOR SEQ ID NO:83:

( i ) SEQUENCE CHARACTERISTICS:
    ( A ) LENGTH: 8 amino acids
    ( B ) TYPE: amino acid
    ( D ) TOPOLOGY: unknown ( i i ) MOLECULE TYPE: peptide ( i x ) FEATURE:
    ( A ) NAME/KEY: Modified-site
    ( B ) LOCATION: 8
    ( D ) OTHER INFORMATION: /note= "R'is terminally linked to
        the carboxyl group of Arg, wherein R' is selected from
        the group consisting of an amide, a lower alkyl ester,
        a cycloalkyl ester, an aryl ester and a heteroaryl ester,
        wherein the aryl or heteroaryl ester is either
        unsubstituted or substituted with a halogen, methoxy,
        amino or alkyl functional group"

( i ) SEQUENCE DESCRIPTION: SEQ ID NO:83:

Thr Thr Ser Gln Val Arg Pro Arg
1               5

( 2 ) INFORMATION FOR SEQ ID NO:84:

( i ) SEQUENCE CHARACTERISTICS:
    ( A ) LENGTH: 8 amino acids
    ( B ) TYPE: amino acid
    ( D ) TOPOLOGY: unknown ( i i ) MOLECULE TYPE: peptide ( i ) FEATURE:
    ( A ) NAME/KEY: Modified-site
    ( B ) LOCATION: 1
    ( D ) OTHER INFORMATION: /note= "R-(C=O)- is terminally
        linked to the amino group of Thr, where R is selected
        from the group consisting of a lower alkyl, a
        cycloalkyl, an aryl, and a heteroaryl, wherein the aryl
        or heteroaryl is either unsubstituted or substituted with
        a halogen, methoxy, amino or alkyl functional group"

( i ) FEATURE:
: ( A ) NAME/KEY: Modified-site
: ( B ) LOCATION: 8
: ( D ) OTHER INFORMATION: /note= "R' is terminally linked to the carboxyl group of Arg, wherein R' is selected from the group consisting of an amide, a lower alkyl ester, a cycloalkyl ester, an aryl ester and a heteroaryl ester, wherein the aryl or heteroaryl ester is either unsubstituted or substituted with a halogen, methoxy, amino or alkyl functional group"

( i ) SEQUENCE DESCRIPTION: SEQ ID NO:84:

Thr Thr Ser Gln Val Arg Pro Arg
1               5

( 2 ) INFORMATION FOR SEQ ID NO:85:

: ( i ) SEQUENCE CHARACTERISTICS:
:: ( A ) LENGTH: 8 amino acids
:: ( B ) TYPE: amino acid
:: ( D ) TOPOLOGY: unknown : ( i i ) MOLECULE TYPE: peptide : ( i ) FEATURE:
:: ( A ) NAME/KEY: Modified-site
:: ( B ) LOCATION: 1
:: ( D ) OTHER INFORMATION: /note= "There is an acetyl group at the amino terminal end of the peptide"

: ( i ) SEQUENCE DESCRIPTION: SEQ ID NO:85:

Thr Thr Ser Gln Val Arg Pro Arg
1               5

( 2 ) INFORMATION FOR SEQ ID NO:86:

: ( i ) SEQUENCE CHARACTERISTICS:
:: ( A ) LENGTH: 8 amino acids
:: ( B ) TYPE: amino acid
:: ( D ) TOPOLOGY: unknown : ( i i ) MOLECULE TYPE: peptide : ( i ) FEATURE:
:: ( A ) NAME/KEY: Modified-site
:: ( B ) LOCATION: 8
:: ( D ) OTHER INFORMATION: /note= "There is an amido group at the carboxyl terminal end of the peptide"

: ( i ) SEQUENCE DESCRIPTION: SEQ ID NO:86:

Thr Thr Ser Gln Val Arg Pro Arg
1               5

( 2 ) INFORMATION FOR SEQ ID NO:87:

: ( i ) SEQUENCE CHARACTERISTICS:
:: ( A ) LENGTH: 8 amino acids
:: ( B ) TYPE: amino acid
:: ( D ) TOPOLOGY: unknown : ( i i ) MOLECULE TYPE: peptide : ( i ) FEATURE:
:: ( A ) NAME/KEY: Modified-site
:: ( B ) LOCATION: 1
:: ( D ) OTHER INFORMATION: /note= "There is an acetyl group at the amino terminal end of the peptide"

: ( i ) FEATURE:
:: ( A ) NAME/KEY: Modified-site
:: ( B ) LOCATION: 8
:: ( D ) OTHER INFORMATION: /note= "There is an amido group at the carboxy terminal end of the peptide"

-continued (i) SEQUENCE DESCRIPTION: SEQ ID NO:87:

Thr Thr Ser Gln Val Arg Pro Arg
1               5

(2) INFORMATION FOR SEQ ID NO:88:

(i) SEQUENCE CHARACTERISTICS:
      (A) LENGTH: 8 amino acids
      (B) TYPE: amino acid
      (D) TOPOLOGY: unknown (ii) MOLECULE TYPE: peptide (xi) SEQUENCE DESCRIPTION: SEQ ID NO:88:

Thr Thr Ser Glu Val Glu Pro Arg
1               5

(2) INFORMATION FOR SEQ ID NO:89:

(i) SEQUENCE CHARACTERISTICS:
      (A) LENGTH: 8 amino acids
      (B) TYPE: amino acid
      (D) TOPOLOGY: unknown (ii) MOLECULE TYPE: peptide (xi) SEQUENCE DESCRIPTION: SEQ ID NO:89:

Thr Thr Glu Glu Val Arg Pro Arg
1               5

(2) INFORMATION FOR SEQ ID NO:90:

(i) SEQUENCE CHARACTERISTICS:
      (A) LENGTH: 8 amino acids
      (B) TYPE: amino acid
      (D) TOPOLOGY: unknown (ii) MOLECULE TYPE: peptide (xi) SEQUENCE DESCRIPTION: SEQ ID NO:90:

Thr Thr Glu Glu Val Glu Pro Arg
1               5

(2) INFORMATION FOR SEQ ID NO:91:

(i) SEQUENCE CHARACTERISTICS:
      (A) LENGTH: 8 amino acids
      (B) TYPE: amino acid
      (D) TOPOLOGY: unknown (ii) MOLECULE TYPE: peptide (xi) SEQUENCE DESCRIPTION: SEQ ID NO:91:

Thr Thr Ser Glu Val Ala Pro Arg
1               5

What is claimed is:

1. A peptide having the amino acid sequence D-Thr-Thr-Ser-Gln-Val-Arg-Pro-Arg (SEQ ID NO 66).

2. A peptide having the amino acid sequence selected from the group consisting of Thr-Xaa-Ser-Gln-Val-Arg-Pro-Arg (SEQ ID NO 75), wherein Xaa is nothing, L-Lys, L-Orn, L-Met, L-Arg, or L-Trp, Thr-Glu-Ser-Gln-Val-Arg-Pro-Arg (SEQ ID NO: 30), Thr-Ala-Ser-Gln-Val-Arg-Pro-Arg (SEQ ID NO:38), and Thr-Leu-Ser-Gln-Val-Arg-Pro-Arg (SEQ ID NO:59), and which peptide exhibits anti-inflammatory activity.

3. A peptide having the amino acid sequence selected from the group consisting of Thr-Thr-Xaa-Gln-Val-Arg-Pro-Arg (SEQ ID NO 76), wherein Xaa is nothing, L-Glu, L-Asp, L-His, L-Lys, L-Orn, or L-Trp, Thr-Thr-Leu-Gln-Val-Arg-Pro-Arg (SEQ ID NO:60), and Thr-Thr-Ala-Gln-Val-Arg-Pro-Arg (SEQ ID NO:39), and which peptide exhibits anti-inflammatory activity.

4. A peptide having the amino acid sequence selected from the group consisting of Thr-Thr-Ser-Xaa-Val-Arg-Pro-Arg (SEQ ID NO 77), wherein Xaa is nothing, L-Lys, L-Orn, L-Arg, L-Asp, L-Glu or L-Met, and

77

Thr-Thr-Ser-Ala-Val-Arg-Pro-Arg (SEQ ID NO:40), and which peptide exhibits anti-inflammatory activity.

5. A peptide having the amino acid sequence selected from the group consisting of Thr-Thr-Ser-Gln-Xaa-Arg-Pro-Arg (SEQ ID NO 78), wherein Xaa is nothing, Thr-Thr-Ser-Gln-Glu-Arg-Pro-Arg (SEQ ID NO:33), and Thr-Thr-Ser-Gln-Lys-Arg-Pro-Arg (SEQ ID NO:54), and which peptide exhibits anti-inflammatory activity.

6. The peptide according to claim 5 wherein the amino acid sequence is Thr-Thr-Ser-Gln-Lys-Arg-Pro-Arg (SEQ ID NO:54).

7. A peptide having the amino acid sequence selected from the group consisting of Thr-Thr-Ser-Gln-Val-Xaa-Pro-Arg (SEQ ID NO 79), wherein Xaa is nothing, Thr-Thr-Ser-Gln-Val-Glu-Pro-Arg (SEQ ID NO:34), Thr-Thr-Ser-Gln-Val-Ala-Pro-Arg (SEQ ID NO:42), and Thr-Thr-Ser-Gln-Val-Leu-Pro-Arg (SEQ ID NO:63), and which peptide exhibits anti-inflammatory activity.

8. The peptide according to claim 7 wherein the amino acid sequence is selected from the group consisting of Thr-Thr-Ser-Gln-Val-Glu-Pro-Arg (SEQ ID NO 34) and Thr-Thr-Ser-Gln-Val-Ala-Pro-Arg (SEQ ID NO 42).

9. A peptide having the amino acid sequence selected from the group consisting of Thr-Thr-Ser-Gln-Val-Arg-Xaa-Arg (SEQ ID NO 80), wherein Xaa is nothing, Thr-Thr-Ser-Gln-Val-Arg-Lys-Arg (SEQ ID NO:56), and Thr-Thr-Ser-Gln-Val-Arg-Glu-Arg (SEQ ID NO:35), and which peptide exhibits anti-inflammatory activity.

10. A peptide having the amino acid sequence selected from the group consisting of Thr-Thr-Ser-Gln-Val-Arg-Pro-Xaa (SEQ ID NO 81), wherein Xaa is nothing, L-Asn, L-Asp, L-Cys, L-Glu, L-Met, L-Ser, or L-Tyr, and Thr-Thr-Ser-Gln-Val-Arg-Pro-Ala (SEQ ID NO:44), and which peptide exhibits anti-inflammatory activity.

11. A peptide having the amino acid sequence R-$Xaa_1$-$Xaa_2$-$Xaa_3$-$Xaa_4$-$Xaa_5$-$Xaa_6$-$Xaa_7$-$Xaa_8$-R" (SEQ ID NO 74), wherein:

R is either H or $R^1$—(C=O)—, wherein R' is selected from the group consisting of a lower alkyl, a cycloalkyl, an aryl and a heteroaryl, wherein the aryl or heteroaryl is either unsubstituted or substituted with a halogen, methoxy, amino or alkyl group;

R" is selected from the group consisting of OH, an amide, a lower alkyl ester, a cycloalkyl ester, an aryl ester and a heteroaryl ester, wherein the aryl ester or heteroaryl ester is either unsubstituted or substituted with a halogen, methoxy, amino or alkyl functional group;

$Xaa_1$ is nothing or L-Thr;

$Xaa_2$ is selected from the group consisting of nothing, L-Thr, L-Lys, L-Orn, L-Met, L-Arg, L-Ser, L-Trp, L-Tyr, L-Cys and L-His;

$Xaa_3$ is selected from the group consisting of nothing, L-Ser, L-Glu, L-Asp, L-Asn, L-Gln, L-Cys, L-His, L-Lys, L-Orn, L-Thr, L-Trp and L-Tyr;

$Xaa_4$ is selected from the group consisting of nothing, L-Gln, L-Lys, L-Orn, L-Arg, L-Asp, L-Cys, L-Glu, L-His, L-Met, L-Ser, L-Thr and L-Tyr;

$Xaa_5$, $Xaa_6$ and $Xaa_7$ are each either nothing or any naturally occurring L-amino acids; and $Xaa_8$ is selected from the group consisting of nothing, L-Arg, L-Lys, L-Orn, L-Asn, L-Asp, L-Cys, L-Glu, L-His, L-Met, L-Ser and L-Tyr;

78 provided that R-$Xaa_1$-$Xaa_2$-$Xaa_3$-$Xaa_4$-$Xaa_5$-$Xaa_6$-$Xaa_7$-$Xaa_8$-R" (SEQ ID NO 74), is a non-cyclic heptapeptide;

and which peptide exhibits anti-inflammatory activity.

12. A derivative of the peptide of claim 11, wherein at least one side chain amine group is acylated or arylated, or one side chain hydroxyl group is esterified to an alkyl group or an aryl group, and which derivative exhibits anti-inflammatory activity.

13. An analog of the peptide of claim 11, wherein said analog contains at least one amino acid mimic, which mimic serves to reduce proteolytic cleavage of the analog as compared to the peptide, and which analog exhibits anti-inflammatory activity.

14. A derivative of a peptide having the amino acid sequence R-$Xaa_1$-$Xaa_2$-$Xaa_3$-$Xaa_4$-$Xaa_5$-$Xaa_6$-$Xaa_7$-$Xaa_8$-R" (SEQ ID NO 74), wherein:

R is either H or R'—(C=O)—, wherein R' is selected from the group consisting of a lower alkyl, a cycloalkyl, an aryl and a heteroaryl, wherein the aryl or heteroaryl is either unsubstituted or substituted with a halogen, methoxy, amino or alkyl group;

R" is selected from the group consisting of OH, an amide, a lower alkyl ester, a cycloalkyl ester, an aryl ester and a heteroaryl ester, wherein the aryl ester or heteroaryl ester is either unsubstituted or substituted with a halogen, methoxy, amino or alkyl functional group;

$Xaa_1$ is L-Thr;

$Xaa_2$ is selected from the group consisting of L-Thr, L-Lys, L-Orn, L-Met, L-Arg, L-Ser, L-Trp, L-Tyr, L-Cys and L-His;

$Xaa_3$ is selected from the group consisting of L-Ser, L-Glu, L-Asp, L-Asn, L-Gln, L-Cys, L-His, L-Lys, L-Orn, L-Thr, L-Trp and L-Tyr;

$Xaa_4$ is selected from the group consisting of L-Gln, L-Lys, L-Orn, L-Arg, L-Asp, L-Cys, L-Glu, L-His, L-Met, L-Ser, L-Thr and L-Tyr;

$Xaa_5$, $Xaa_6$ and $Xaa_7$ are each any naturally occurring L-amino acids; and $Xaa_8$ is selected from the group consisting of L-Arg, L-Lys, L-Orn, L-Asn, L-Asp L-Cys, L-Glu, L-His, L-Met, L-Ser and L-Tyr;

provided that R-$Xaa_1$-$Xaa_2$-$Xaa_3$-$Xaa_4$-$Xaa_5$-$Xaa_6$-$Xaa_7$-$Xaa_8$-R" (SEQ ID NO 74) is an octapeptide;

and further provided that "R-$Xaa_1$-$Xaa_2$-$Xaa_3$-$Xaa_4$-$Xaa_5$-$Xaa_6$-$Xaa_7$-$Xaa_8$-R" (SEQ ID NO 74) is not Thr-Thr-Ser-Gln-Val-Arg-Pro-Arg (SEQ ID NO 1);

wherein said peptide is derivatized by covalently linking an amine group of a first amino acid residue of the peptide to a carboxyl group of a second, non-adjacent amino acid residue of the peptide to form a cyclized derivative of the peptide, and which derivative exhibits anti-inflammatory activity.

15. A derivative of a peptide having the amino acid sequence R-$Xaa_1$-$Xaa_2$-$Xaa_3$-$Xaa_4$-$Xaa_5$-$Xaa_6$-$Xaa_7$-$Xaa_8$-R" (SEQ ID NO 74), wherein:

R is either H or R'—(C=O)—, wherein R' is selected from the group consisting of a lower alkyl, a cycloalkyl, an aryl and a heteroaryl, wherein the aryl or heteroaryl is either unsubstituted or substituted with a halogen, methoxy, amino or alkyl group;

R" is selected from the group consisting of OH, an amide, a lower alkyl ester, a cycloalkyl ester, an aryl ester and a heteroaryl ester, wherein the aryl ester or heteroaryl ester is either unsubstituted or substituted with a halogen, methoxy, amino or alkyl functional group:

Xaa₁ is L-Thr;

Xaa₂ is selected from the group consisting of L-Thr, L-Lys, L-Orn, L-Met, L-Arg, L-Ser, L-Trp, L-Tyr, L-Cys and L-His;

Xaa₃ is selected from the group consisting of L-Ser, L-Glu, L-Asp, L-Asn, L-Gln, L-Cys, L-His, L-Lys, L-Orn, L-Thr, L-Trp and L-Tyr;

Xaa₄ is selected from the group consisting of L-Gln, L-Lys, L-Orn, L-Arg, L-Asp, L-Cys, L-Glu, L-His, L-Met, L-Ser, L-Thr and L-Tyr;

Xaa₅, Xaa₆ and Xaa₇ are each any naturally occurring L-amino acids; and

Xaa₈ is selected from the group consisting of L-Arg, L-Lys, L-Orn, L-Asn, L-Asp, L-Cys, L-Glu, L-His, L-Met, L-Ser and L-Tyr;

provided that R-Xaa₁-Xaa₂-Xaa₃-Xaa₄-Xaa₅-Xaa₆-Xaa₇-Xaa₈-R" (SEQ ID NO 74) is an octapeptide;

wherein said peptide is derivatized by the formation of one or more intramolecular disulfide bridges, and which derivative exhibits anti-inflammatory activity.

16. The peptide of claim 3, having the amino acid sequence Thr-Thr-Glu-Gln-Val-Arg-Pro-Arg (SEQ ID NO 31).

17. The peptide of claim 4, having the amino acid sequence Thr-Thr-Ser-Glu-Val-Arg-Pro-Arg (SEQ ID NO 32).

18. The peptide of claim 7, having the amino acid sequence Thr-Thr-Ser-Gln-Val-Ala-Pro-Arg (SEQ ID NO 42).

19. The peptide of claim 7, having the amino acid sequence Thr-Thr-Ser-Gln-Val-Glu-Pro-Arg (SEQ ID NO 34).

20. A peptide having the amino acid sequence selected from the group consisting of Thr-Thr-Ser-Glu-Val-Glu-Pro-Arg (SEQ ID NO 88), Thr-Thr-Glu-Glu-Val-Arg-Pro-Arg (SEQ ID NO 89), Thr-Thr-Glu-Glu-Val-Glu-Pro-Arg (SEQ ID NO 90), and Thr-Thr-Ser-Glu-Val-Ala-Pro-Arg (SEQ ID NO 91), and which peptide exhibits anti-inflammatory activity.

21. A pharmaceutical composition, comprising the peptide, peptide derivative or peptide analog of claim 2, 3, 4, 5, 7, 9, 10, 11, 12, 13, 14 15, or 1 and a pharmaceutically acceptable carrier.

22. A method of inhibiting an inflammatory response that is associated or caused by a disease selected from the group consisting of ulcerative colitis, rheumatoid arthritis, scleroderma, mixed connective tissue disease and systemic lupus erythematosus, in a tissue of a subject in need of such treatment, comprising exposing the subject to an effective amount of a peptide selected from the group consisting of:

Thr-Thr-Ser-Gln-Val-Arg-Pro-Arg (SEQ. ID NO: 1);

Val-Lys-Thr-Thr-Ser-Gln-Val-Arg-Pro-Arg (SEQ. ID NO: 2);

Ser-Gln-Val-Arg-Pro-Arg (SEQ. ID NO: 3);

Val-Arg-Pro-Arg (SEQ. ID NO: 4);

Thr-Thr-Ser-Gln-Val-Arg-Pro-Arg-His-Ile-Thr (SEQ. ID NO: 5);

Thr-Thr-Ser-Gln-Val (SEQ. ID NO: 6);

Thr-Ser-Gln-Val-Arg (SEQ. ID NO: 7); and

Thr-Thr-Ser-Gly-Ile-His-Pro-Lys (SEQ. ID NO: 8).

23. A method of inhibiting an inflammatory response in a tissue of a subject in need of such treatment, comprising exposing the subject to an effective amount of the peptide, peptide derivative or peptide analog of claim 2, 3, 4, 5, 7, 9, 10, 11, 12, 13, 14 15, or 1.

24. The method of claim 23 in which the inflammatory response is associated or caused by an autoimmune disease selected from the group consisting of ulcerative colitis, rheumatoid arthritis, scleroderma, mixed connective tissue disease, systemic lupus erythematosus and inflammatory lung disease.

* * * * *